US008867046B2

(12) United States Patent
Jeys et al.

(10) Patent No.: US 8,867,046 B2
(45) Date of Patent: Oct. 21, 2014

(54) METHOD AND APPARATUS FOR MEASURING A POSITION OF A PARTICLE IN A FLOW

(71) Applicant: Massachusetts Institute of Technology, Cambridge, MA (US)

(72) Inventors: Thomas H. Jeys, Lexington, MA (US); Antonio Sanchez-Rubio, Lexington, MA (US); Ronald H. Hoffeld, Cambridge, MA (US); Jonathan Z. Lin, Winchester, MA (US); Nicholas M. F. Judson, Baltimore, MD (US); George S. Haldeman, Melrose, MA (US); Vincenzo Daneu, Woburn, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/662,197

(22) Filed: Oct. 26, 2012

(65) Prior Publication Data

US 2013/0077096 A1   Mar. 28, 2013

Related U.S. Application Data

(63) Continuation of application No. 12/851,866, filed on Aug. 6, 2010, now Pat. No. 8,319,965, which is a continuation of application No. 11/804,593, filed on May 18, 2007, now Pat. No. 7,821,636, which is a continuation-in-part of application No. 11/804,589, filed on May 18, 2007, now Pat. No. 7,772,579.

(60) Provisional application No. 60/802,088, filed on May 18, 2006, provisional application No. 60/927,832, filed on May 4, 2007, provisional application No. 60/802,087, filed on May 18, 2006.

(51) Int. Cl.
*G01B 11/14* (2006.01)
*G01B 11/00* (2006.01)
*G01N 21/53* (2006.01)
*G01N 15/14* (2006.01)

(52) U.S. Cl.
CPC .............. *G01N 21/53* (2013.01); *G01B 11/002* (2013.01); *G01N 2015/145* (2013.01); *G01N 15/1459* (2013.01)
USPC ............ 356/614; 250/575; 356/615; 382/103

(58) Field of Classification Search
CPC ................................. G01N 21/53; G01B 11/02
USPC .......... 250/573–575; 356/343, 621, 623, 615; 382/103
See application file for complete search history.

(56) References Cited

U.S. PATENT DOCUMENTS

| 4,643,566 A | 2/1987 | Ohe et al. |
| 5,282,151 A | 1/1994 | Knollenberg |

(Continued)

FOREIGN PATENT DOCUMENTS

| DE | 39 31 119 C1 | 4/1991 |
| DE | 198 34 583 C1 | 12/1999 |

(Continued)

OTHER PUBLICATIONS

R. M. Huffaker, "Laser Doppler detection systems for gas velocity measurement," *Appl. Opt.* vol. 9, No. 1, 1026-1039 (Jan. 1970).

(Continued)

*Primary Examiner* — Tarifur Chowdhury
*Assistant Examiner* — Iyabo S Alli
(74) *Attorney, Agent, or Firm* — Hamilton, Brook, Smith & Reynolds, P.C.

(57) ABSTRACT

A method and an apparatus of measuring a position of a particle in a flow are disclosed. An embodiment of the method comprises temporally modulating and spatially pattering an illumination beam propagating along a first dimension, passing a particle across the modulated illumination beam, detecting a temporal profile of scattered light produced by the particle's passing through the modulated illumination beam, and determining the position of the particle based, in part, on the temporal profile of the detected scattered light.

14 Claims, 20 Drawing Sheets

(56) References Cited

U.S. PATENT DOCUMENTS

| | | | |
|---|---|---|---|
| 5,793,478 | A | 8/1998 | Rader et al. |
| 5,883,707 | A | 3/1999 | Arndt et al. |
| 5,920,388 | A * | 7/1999 | Sandberg et al. ............. 356/315 |
| 6,867,410 | B2 | 3/2005 | Sasaki et al. |
| 7,471,393 | B2 * | 12/2008 | Trainer ......................... 356/336 |
| 7,772,579 | B2 | 8/2010 | Herzog et al. |
| 7,821,636 | B2 | 10/2010 | Jeys et al. |
| 7,920,261 | B2 | 4/2011 | Jeys et al. |
| 8,319,965 | B2 | 11/2012 | Jeys et al. |
| 2001/0040214 | A1 | 11/2001 | Friedman et al. |
| 2002/0122167 | A1 | 9/2002 | Riley et al. |
| 2005/0122522 | A1 | 6/2005 | Padmanabhan et al. |
| 2006/0066837 | A1 | 3/2006 | Ortyn et al. |
| 2006/0204071 | A1 | 9/2006 | Ortyn et al. |
| 2008/0030716 | A1 | 2/2008 | Jeys et al. |
| 2008/0068605 | A1 | 3/2008 | Herzog et al. |
| 2009/0219530 | A1 | 9/2009 | Mitchell et al. |

FOREIGN PATENT DOCUMENTS

| | | |
|---|---|---|
| DE | 199 26 494 A1 | 12/2000 |
| DE | 199 54 702 A1 | 5/2001 |
| EP | 0 467 127 A2 | 1/1992 |
| JP | 61-29737 | 10/1986 |
| WO | WO 98/41876 | 9/1998 |
| WO | WO 01/79861 A1 | 10/2001 |
| WO | WO 2005/090945 A1 | 9/2005 |
| WO | WO 2007/136818 | 11/2007 |
| WO | WO 2008/010870 A2 | 1/2008 |
| WO | WO 02/088673 A2 | 11/2008 |
| WO | WO 2009/102299 A1 | 8/2009 |

OTHER PUBLICATIONS

D.T. Suess and K. A. Prather, "Mass spectrometry of aerosols", *Chem. Rev.* 99, 3007-3035 (1999).

Y.L. Pan, S. Holler, R. K. Chang, S. C. Hill, R. G. Pinnick, S. Niles, and J. R. Bottiger, "Single-shot fluorescence spectra of individual micrometer-sized bioaerosols illuminated by a 351- or a 266-nm ultraviolet laser," *Opt. Lett.* vol. 24, No. 1, pp. 116-118 (Jan. 1999).

K. Davitt, Y.-K. Song, W. Patterson, III, A. Nurmikko, M. Gherasimova, J. Han, Y.-L. Pan, and R. Chang, "290 and 340 nm UV LED arrays for fluorescence detection from single airborne particles," *Opt. Express* vol. 13, No. 23, pp. 9548-9555 (Nov. 2005).

D. R. Burnham and D. McGloin, "Holographic optical trapping of aerosol droplets," *Opt. Express* vol. 14, No. 9, pp. 4175-4181 (2006).

K. G. Bartlett and C. Y. She, "Single-particle correlated time-of-flight velocimeter for remote wind-speed measurement," *Opt. Lett.* vol. 1, No. 5, pp. 175-177 (Nov. 1977).

William D. Herzog, Shane M. Tysk, David W. Tardiff, Gregory G. Cappiello, Jasaon M. Jong, Thomas H. Jeys, Ronald H. Hoffeld, Antonio Sanchez and Vincenzo Daneu, "Measurement of aerosol-particle trajectories using a structured laser beam," *Appl. Opt.* vol. 46, No. 16, pp. 3150-3155 (Jun. 2007).

International Search Report and Written Opinion of the International Searching Authority from PCT/US2008/001793 mailed Nov. 21, 2008.

International Search Report and Written Opinion from PCT/US2007/012034 mailed Feb. 7, 2008.

International Search Report and Written Opinion from PCT/US2007/012047 mailed May 7, 2008.

International Preliminary Report on Patentability in International Application No. PCT/US2007/012047, 6 pages, mailed Nov. 18, 2008.

International Preliminary Report on Patentability in International Application No. PCT/US2007/012034, 9 pages, mailed Nov. 18, 2008.

International Preliminary Report on Patentability in International Application No. PCT/US2008/001793, 9 pages, mailed Aug. 17, 2010.

P. Lilienfeld, et al., "Development of a Prototype Fibrous Aerosol Monitor," *Am. Ind. Hyg. Assoc. J.* 40(4), 270-282 (1979).

* cited by examiner

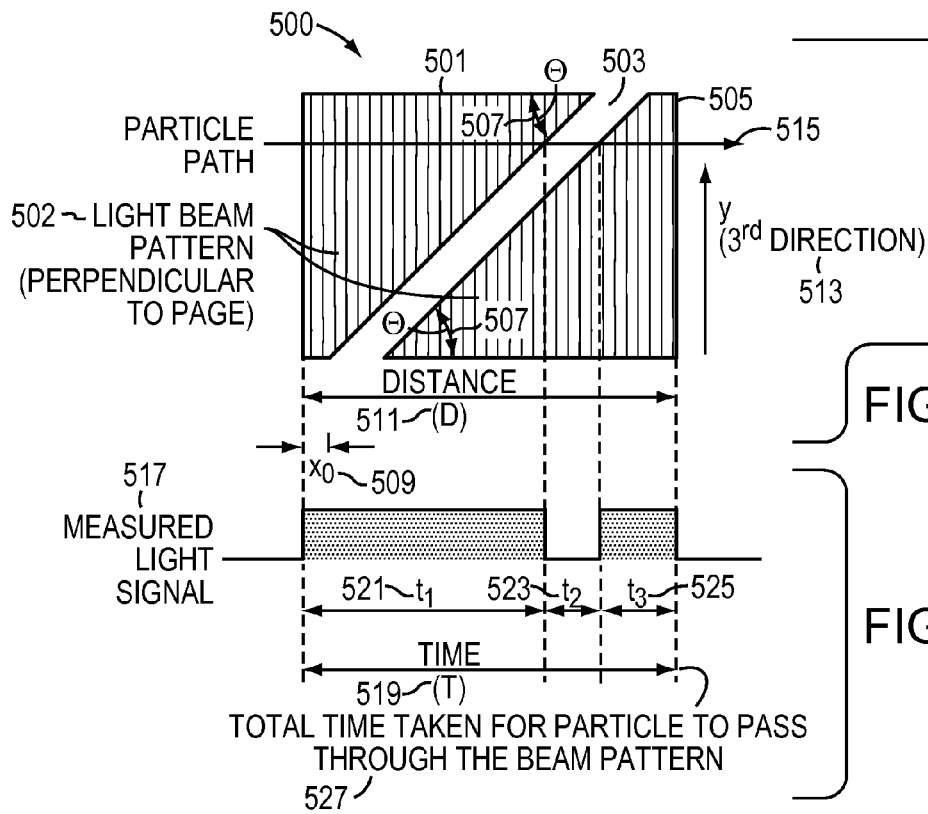
FIG. 5A
FIG. 5B
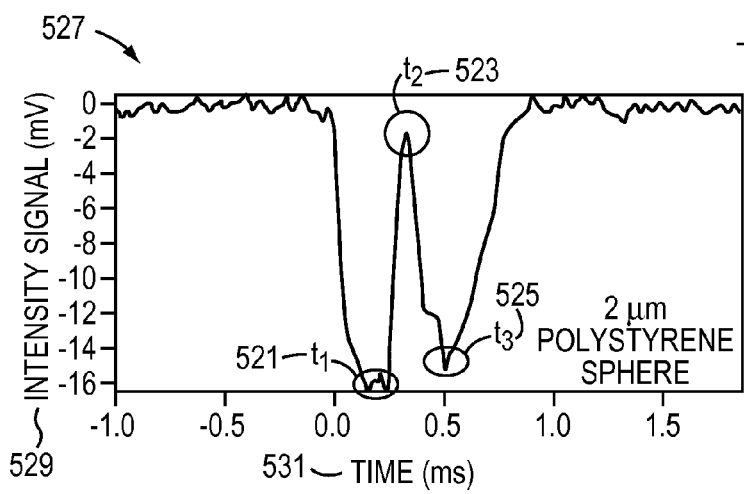
FIG. 5C

MASKING ELEMENT FEATURING A PATTERN
OF VARYING POLARIZATION

METHOD AND APPARATUS FOR MEASURING A POSITION OF A PARTICLE IN A FLOW

RELATED APPLICATIONS

This application is a continuation of U.S. application Ser. No. 12/851,866, filed Aug. 6, 2010, which is a continuation of U.S. application Ser. No. 11/804,593, filed May 18, 2007, now U.S. Pat. No. 7,821,636, which claims the benefit of U.S. Provisional Application No. 60/802,088, filed on May 18, 2006, and is also a continuation-in-part of U.S. application Ser. No. 11/804,589, filed May 18, 2007, now U.S. Pat. No. 7,772,579, which also claims the benefit of U.S. Provisional Application Nos. 60/927,832, filed May 4, 2007 and 60/802,087, filed on May 18, 2006.

The entire teachings of the above applications are incorporated herein by reference.

GOVERNMENT SUPPORT

This invention was made with government support under Contract No. F19628-00-C-0002/MIT-LL-22 awarded by the U.S. Air Force. The government has certain rights in the invention.

BACKGROUND OF THE INVENTION

The ability to detect and classify small particles in a fluid stream has been of great use in many fields. For example, the detection of harmful particles or biological agent particles in air (outdoors or inside a building) or in water (a city water supply) may require monitoring the air or water for such particles.

SUMMARY OF THE INVENTION

Aerosol and hydrosol particle detection systems typically do not determine the exact location of an individual particle as it passes through the detection system sample volume. However, knowledge of the exact particle location has several advantages. These advantages include correction of systematic particle measurement errors due to variability of the particle position within the sample volume, targeting of particles based on position, capture of particles based on position, reduced system energy consumption and reduced system complexity.

An apparatus and method for use for detecting a location of a particle in a fluid stream is described herein. In one example embodiment, the apparatus for measuring a position of a particle in a flow comprises a light source that may be used to generate an illuminating beam to travel in a first dimension and define an illumination pattern in second and third dimensions. The apparatus may further comprise a light detector to detect a temporal profile of scattered light (including elastic scattering, luminescence, and/or Raman scattering) produced by the particle's passing through the illumination pattern in the second dimension. The apparatus may also include a processing unit, coupled to the light detector, to determine the position of the particle, in the third dimension relative to the illumination pattern, based on the temporal profile of the scattered light and a geometrical relationship of the illumination pattern.

The apparatus may further include a masking element in optical arrangement with the light source. The masking element may cause the illuminating beam to define a plurality of regions of the illumination pattern, where at least two regions may comprise varying intensities or polarizations. A specific example of the illuminating beam defining at least two regions of varying intensities of the illumination pattern is where at least one of the regions of the illumination pattern has a measurably different intensity than any of the other regions (i.e., a zero or substantially zero beam intensity).

In at least one example embodiment, the light source may be a first light source, the illuminating beam may be a first illuminating beam, the illuminating pattern may be a first illuminating pattern, the temporal profile may be a first temporal profile, and the scattered light may be a first scattered light. Thus, the apparatus may also include a second light source, which may generate a second illuminating beam to travel in a third dimension, the illuminating beam may define a second illumination pattern in first and second dimensions. The detector may further detect a second temporal profile caused by a second scattered light produced by the particle's passing through the second illuminating pattern. The processing unit may be configured to determine the position of the particle, in the first dimension relative to the second illumination pattern, which may be based on the second temporal profile of the second scattered light and a geometrical relationship of the second illumination pattern.

In another example embodiment, the apparatus may further comprise a modulator to modulate the intensity of the illuminating beam and the intensity of a second illuminating beam. The detector may be a first detector, and the apparatus may further comprise a second detector configured to detect the second temporal profile. The apparatus may also comprise a coding element configured to code distinctly the illumination pattern and the second illumination pattern.

In some example embodiments, the first and second light sources of the apparatus may be configured to illuminate the first illuminating beam and the second illuminating beam at different wavelengths. The apparatus may also comprise a polarizer, in optical arrangement with the light source to distinctly polarize the first illuminating beam and the second illuminating beam.

In another embodiment, the apparatus may further include a patterned optical block. The patterned optical block may comprise a plurality of blocking regions that may be positioned to receive the scattered light. The apparatus may comprise a light shield to shield the illuminating beam, in a manner allowing the scattered light to be received by the optical block, and may further comprise a focusing element to focus the scattered light onto the optical block. The detector may detect a combined temporal profile that may be produced by the particle's passing through the illumination pattern and the plurality of blocking regions on the optical block. The processing unit may determine the position of the particle, in the first dimension relative to the illumination pattern, that may be based on the combined temporal profile of the light scattering.

The processing unit may be configured to measure a relative amount of light of the combined temporal profile that may be blocked from the plurality of blocking regions with respect to an amount of light unblocked by the plurality of blocking regions. The apparatus may also comprise a calculation unit to determine a normalization or correction value, which may be based on a measurement from a standard particle at a known position, to apply to subsequent measurements of nonstandard particles at this same known position.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 5A, 5B and 5C are a depiction of an example illumination pattern and measured signal produced by detecting particles by the systems illustrated in FIGS. 1A and 1B;

DETAILED DESCRIPTION OF THE INVENTION

A description of example embodiments of the invention follows.

Figure 1:
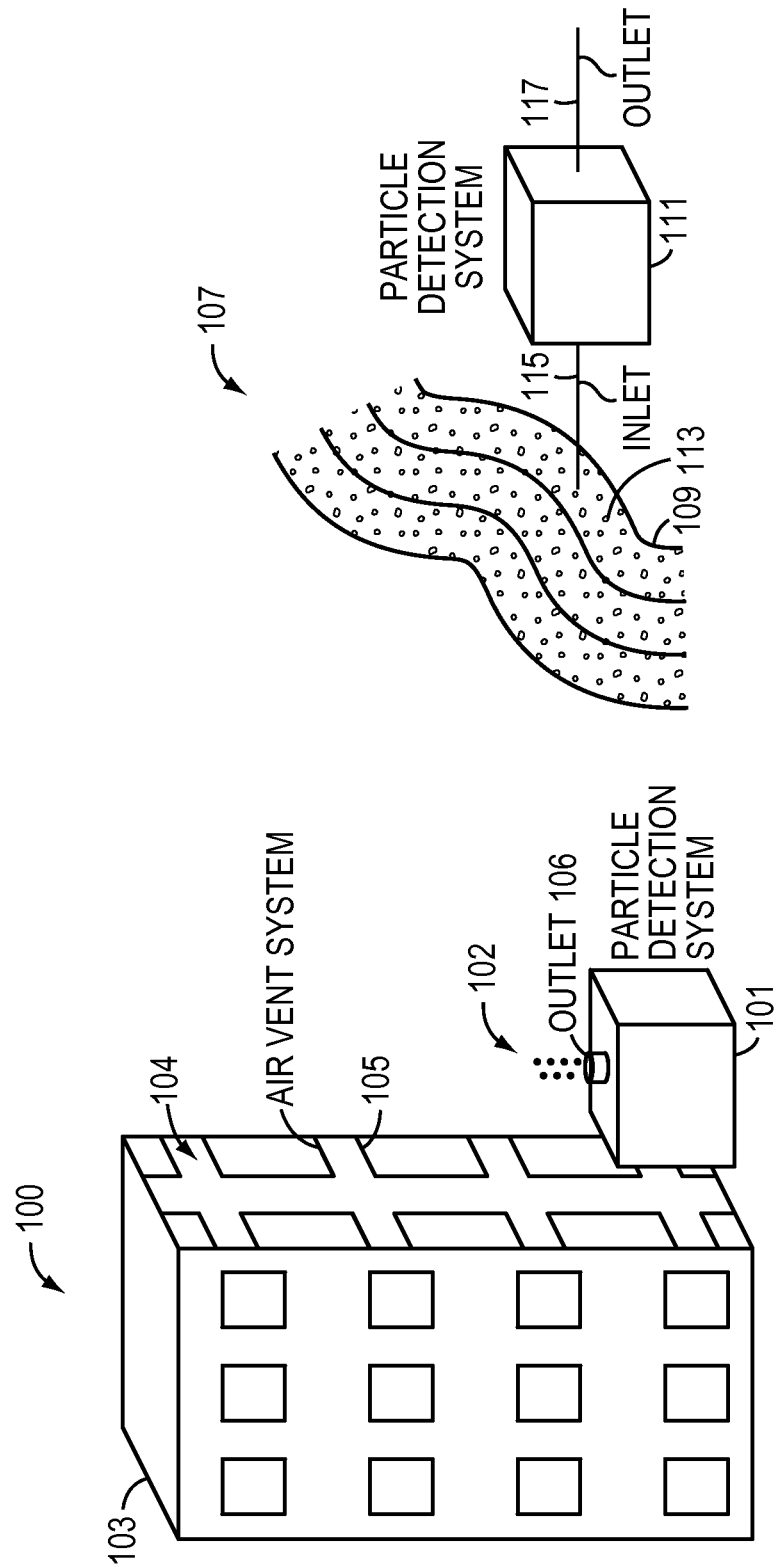
FIGS. 1A and 1B are diagrams with examples of particle detection systems.

FIG. 1A provides an example 100 of a particle detection system 101. The particle detection system 101 may be situated to detect particles 104 in an airvent system 105 of a building 103. The particle detection system 101 includes an inlet (not shown) in which an airflow enters the particle detection system 101. An outlet 106 of the particle detection system 101 may be used as a pathway to shunt the airflow if particles 102 detected are deemed unsafe for breathing. Otherwise, the airflow can continue into the airvent system 105.

As another example, a liquid stream may also need to be evaluated. For instance, a water reservoir may need to be continuously monitored to ensure harmful particles are not introduced into a water supply. FIG. 1B provides an example 107 of a particle detection system 111 detecting particles 113 in a liquid stream 109. The particle detection system 111 may include an inlet 115 used to supply a sample of the liquid flow 109 to the particle detection system 111. Once the liquid flow 109 has been checked for a presence of foreign particles, an outlet 117 may be used to remove the sample from the particle detection system 111.

Figure 2:
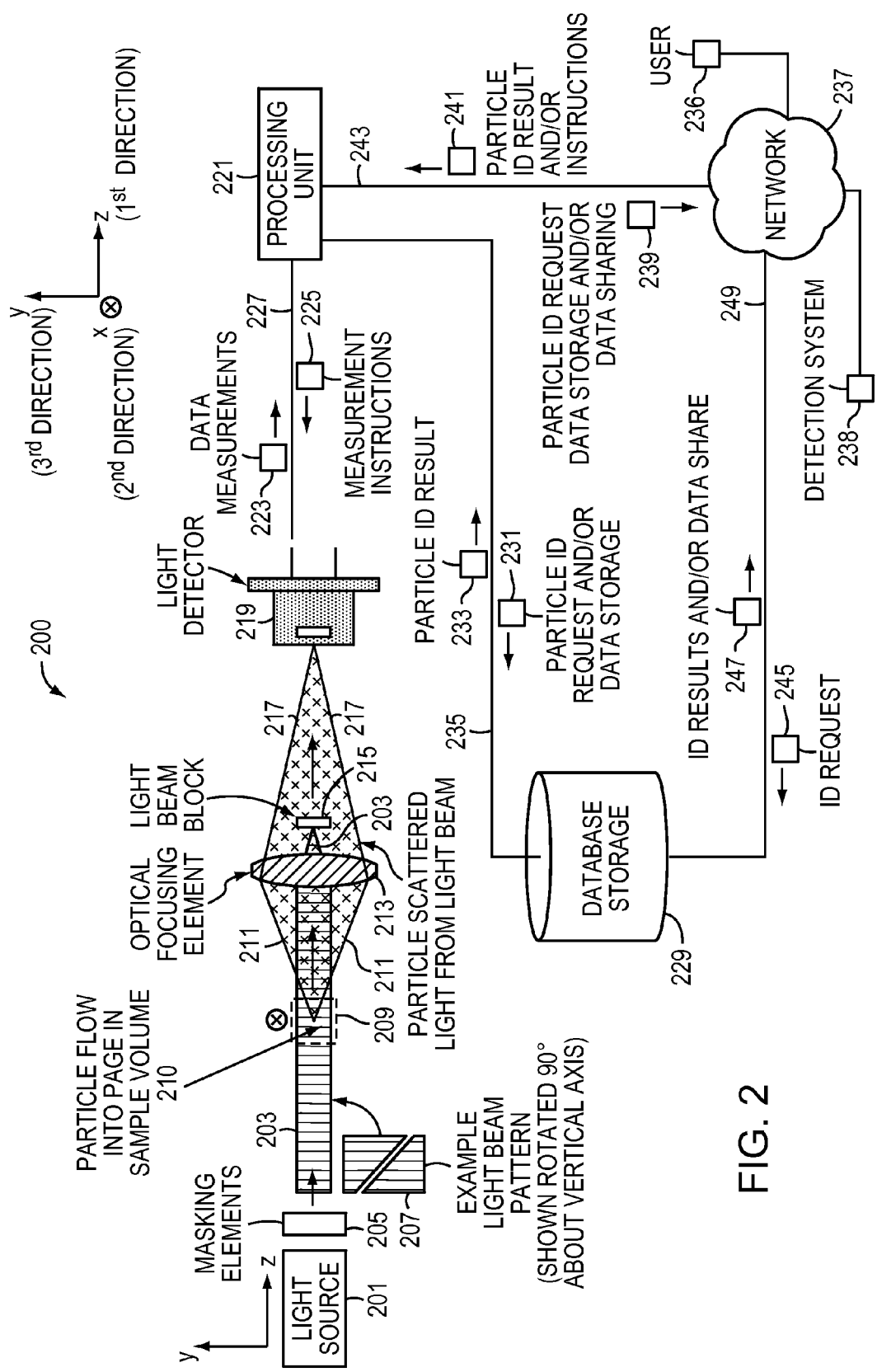
FIG. 2 is a schematic diagram of a patterned beam particle detection system for determining a position of a particle in one dimension, according to an embodiment of the present invention.
Figure 3:
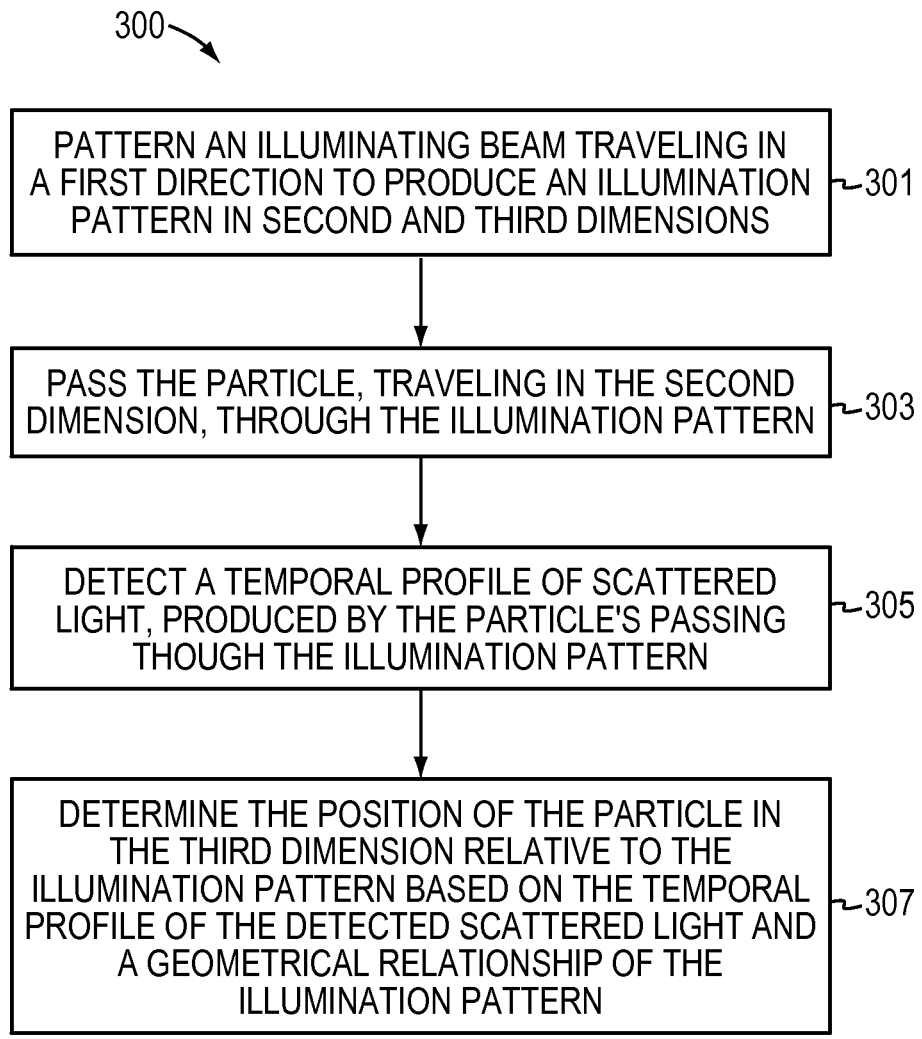
FIG. 3 is a flow diagram of an overview of operative steps of the detection system of FIG. 2.

FIG. 2 provides an example of a particle detection system 200 according to an embodiment of the present invention. FIG. 3 shows a flow diagram 300 of an overview of operations that may be taken by the detection system 200. Referring to FIG. 2 with references to FIG. 3, the particle detection system 200 may include a light source 201 configured to emit a propagating beam 203, also referred to herein as an "illuminating light beam," traveling in the z dimension, or a first dimension. A masking element 205 may be coupled to the light source 201 to produce a light beam pattern 207 also referred to herein as an "illuminating pattern," in x and y dimensions, or second and third dimensions, respectively (FIG. 3, 301). It should be appreciated that the light beam 207 shown in FIG. 2 is rotated 90 degrees about its vertical axis as represented in the Figure. It should also be appreciated that instead of the light beam pattern shown (207) any other light beam pattern may be employed in the detection system 200.

The propagating light beam 203 defines the beam pattern 207 at a sample volume 209 within a particle flow 210. The sample volume 209 may be configured to "receive" the flow in the x axis, or the second dimension. As the particles (not shown) in the sample volume 209 pass through the propagating beam 203, defining the beam pattern 207 (FIG. 3, 303), a diverging light scattering 211 is produced as a result of a collision of photons with the particles passing through the beam pattern 207.

The diverging light scattering 211 has a temporal profile that is a function of the beam pattern 207. For example, for the beam pattern 207, the temporal profile exhibits a first period of signal (i.e., scattering), short period of no or very low signal as the particle passes through the gap in the beam pattern, and then a second period of signal. Accordingly, the temporal profile has a timing indicative of the particle's position in the sample volume 209 in the y, or third, dimension. An optical focusing element 213 may be used to focus the produced diverging scattered light 211, resulting in converging scattered light 217. An optical beam blocker 215 may be used to block the propagating beam 203, thereby preventing the propagating beam 203 from directly reaching the light detector 219 and, thus, preventing detector saturation. The converging scattering light 217 may be focused onto the light detector 219 for detection (FIG. 3, step 305).

In this example embodiment, the light detector 219 is coupled to a processing unit 221. The light detector 219 may be configured send data measurements 223 to the processing unit 221 in the form of an analog electrical signal. The processing unit 221 may be configured to determine the position of the particle in the third dimension, relative to the illumination pattern 207, based on the temporal profile of the detected scattered light 217 (FIG. 3, step 307). The processing unit 221 may send measurement instructions 225 to the light detector 219 in the case of intelligent, programmable configurable. The measurement instructions 225 may include, for example, on/off instructions. The light detector 219 and the processing unit 221 may be connected via a connection link 227. It should be appreciated that the connection link 227 may be a wired, optical, or wireless connection, or any other data transfer connection known in the art.

The processing unit 221 may also be connected to a database storage 229. The processing unit 221 may send the database storage 229 a particle identification request, and/or a data storage request 231. The data storage request 231 may include the data measurements 223, or representation thereof, provided by the light detector 219. The particle identification request may include a request to compare information stored in the database storage 229 with the obtained data measurements 223, optionally for the purpose of classifying and identifying the particles in the sample volume 209. The database storage 229 may send a particle identification result 233 to the processing unit 221. The particle identification result 233 may comprise a listing of possible particle matches with respect to the data measurements 223.

The processing unit 221 may also be coupled to a network 237. The processing unit 221 may send a particle identification request, a data storage request, and/or a data sharing request 239 to the network 237. The particle identification request and data sharing request 239 may be similar to the request 231 sent to the database storage 229. The data sharing request 239 may be a request to share data with a user 236 that may be connected to the network 237, or another detection system 238 that may be connected to the network 237. The network 237 or, more specifically, a server or other network element (not shown) connected to the network 237, may also send a message 241 in the form of particle identification results, similar to the result 233 sent by the database storage 229, or instructions to the processing unit 221. The instructions 241 may be comprise measurement instructions similar to the instructions 225 sent to the light detector 219.

The database storage 229 and the network 237 may also include a bidirectional data transfer connection 249. The database storage 229 may send identification results and/or a data sharing request 247 to the network 237. The network 237 may send an identification request 245 to the database storage 229. It should be appreciated that the data transfer connections 235, 243, and 249 between the processing unit and the data storage, the processing unit and the network, and the network and the data storage, respectively, may include or be supported by any data transmission link known in the art. It should also be appreciated that the configuration shown in FIG. 2 of the particle detection system 200 is merely an example. Any other dimensional configuration may be employed, preferably with the first, second, and third dimensions orthogonal to one another.

Figure 4:
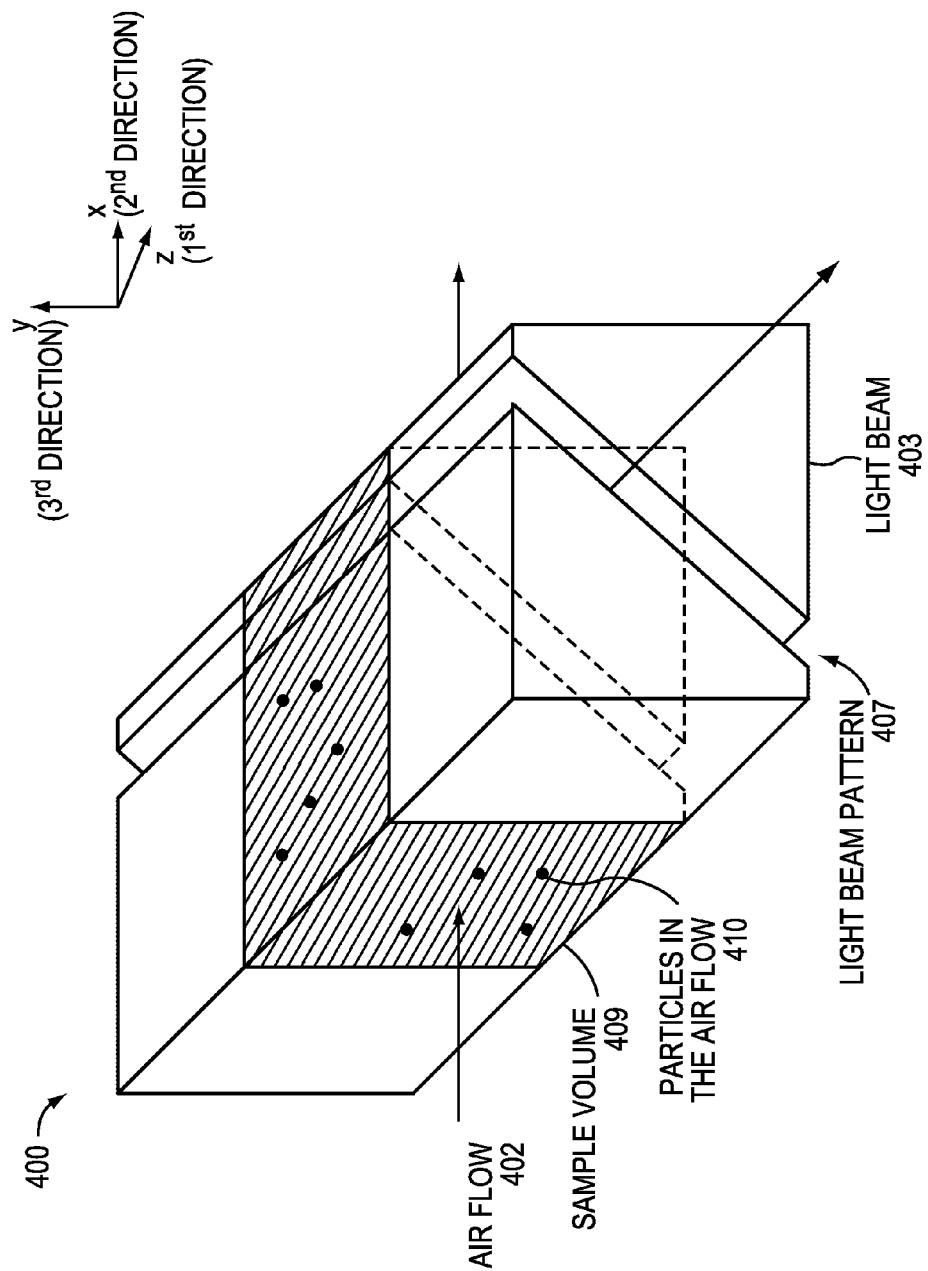
FIG. 4 is a perspective view of an example patterned beam, defining an illumination pattern, illuminating particles in a sample volume of a flow, according to an embodiment of the present invention.

FIG. 4 provides an expanded view 400 of the intersection of the particle air flow 402 and the propagating light beam 403, resulting in a sample volume 409. The propagating light beam 403 may be configured to travel in the z, or first, dimension. As is shown in FIG. 4, the propagating light beam 403 may comprise a light beam pattern 407, similar to the pattern 207 shown in FIG. 2. The light beam pattern 407 may, for example, be defined by a square shaped beam with a center diagonal region having an intensity that is substantially equal to zero or substantially less than the intensity of the surrounding portion(s) of the light beam pattern. The particle air flow 402 may be transmitted in the x, or second, dimension. The sample volume 409 may include any number of particles 410 traveling in the particle air flow. However, it is expected that only one particle at a time will pass through the sample volume 409 at a time or, if more than one particle passes through at a time, they pass through at positions sufficiently distinguishable from each other. It should be appreciated that any geometrical configuration may be employed, provided that the first, second, and third dimensions are orthogonal to each other, in a preferred embodiment.

FIG. 5A provides a detailed schematic diagram 500 of an example light beam pattern 502. The light beam pattern 502 may be formed with different regions of varying intensity. For example, the pattern 502 may include a first region 501, second region 503, and third region 505, with the second region 503 having an intensity that may be measurably less (e.g., 5%, 20%, 50%, 80%, or 100% less) than the intensity of the first and/or third regions 501, 505, respectively. An angle θ 507 defines a sloping of the diagonal second region 503 in this example embodiment. A label '$x_0$' 509 represents the smallest distance a particle (not shown) may pass through the first region 501 before reaching the second region 503. The light beam pattern 502 may be defined by a total distance (D) 511. A position of the particle in the y, or a third, dimension 513 represents a transverse location of the particle in a particle path 515. The transverse location y may be obtained using the geometrical properties of the beam pattern 502 and the temporal profile (described in reference to FIG. 5B below) produced by the particle's passing through the light beam pattern 502 and the geometric properties of the beam pattern.

FIG. 5B represents an example of a measured light signal produced by a particle in the particle path 515 traveling through the beam pattern 502. The measured light signal 515 may comprise three distinct portions. The first portion, labeled $t_1$, 521 represents the time the particle in the particle path 515 took to pass through the first region 501 of the light beam pattern 502. As the particle in the particle path 515 passes through the first region 501 of the beam pattern 502, the particle may produce a scattered light, of an intensity represented as a signal level in the region $t_1$ 521 of the measured light signal 517. As the particle in the particle path 515 passes through the second region 503 of the light pattern 502, no scattered light, or a substantially small amount of scattered light, may be produced due to the low intensity of the second region 503. Therefore, the region labeled as $t_2$ 523 of the measured light signal 517 has a very low intensity reading as compared to that of $t_1$ 521. The region labeled as $t_3$ 525 is a representation of the measured scattered light produced by the particle in the particle path 515 passing through the third region 505 of the light beam pattern 502. As expected, the signal reading in the region $t_3$ 525 is greater than that of $t_2$ 523, since the third region of the pattern 505 has a greater intensity than that of the second region 503.

It should be understood that the intensities of the light beam pattern 502 may be inverted such that the first and third regions 501, 505 are dimmer (i.e., have less intensity) than the second region 503. In this alternative light beam pattern 502 example, the measurements at $t_1$, $t_2$, and $t_3$ are based on the inverted levels of intensity. The relative timing is dependent only on the geometry of the intensity pattern 502. The absolute timing additionally depends on the velocity of the particle through the pattern 502.

FIG. 5C is a graphical representation 527 of the measured light signal 517 from a real particle. The graphical representation 527 is a plot of the intensity signal measured in millivolts (mv) 529 versus the entire time the particle passed through the light beam pattern 502, measured in milliseconds (ms) 531. The time signals $t_1$ 521 and $t_3$ 525 include high intensity signal readings since the first and third regions 501 and 505, respectively, of the light beam pattern 502 have light with a substantial greater intensity than that of the second region 503, represented by the intensity reading $t_2$ 523. Therefore, the first and third regions 501 and 505 produce a greater amount of scattered light when the particle passes through. The measurement $t_2$ 523 provides a very low intensity signal reading in this example due to the fact that the light intensity of the second region 503 is substantially less than the first and third regions 501 and 505, respectively, therefore producing a lesser amount of scattered light when the particle passes through it.

Figure 6A:
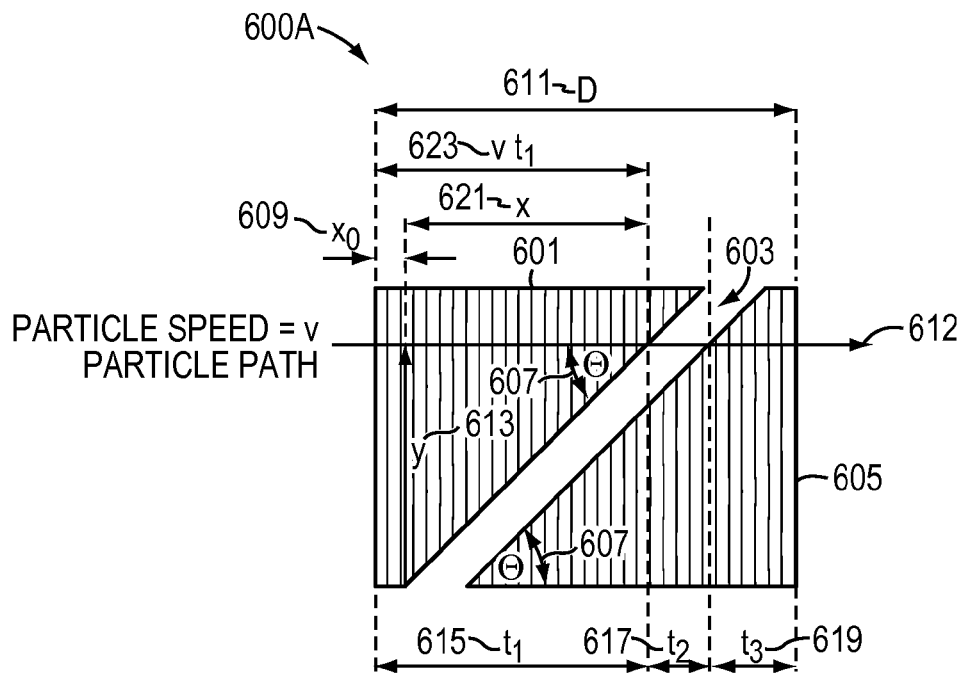
FIGS. 6A and 6B are diagrams of example geometrical configurations of the illumination pattern.
Figure 6B:
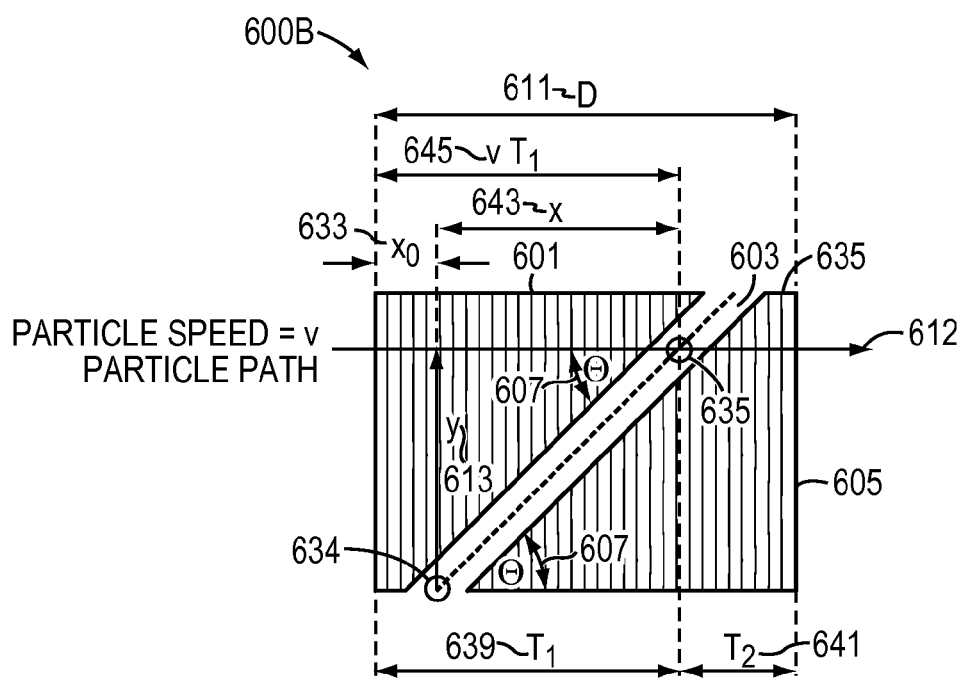

FIGS. 6A and 6B provide a depiction of the geometric relationship between the particle in the particle path and the patterned light beam 600a. In FIG. 6A the patterned beam 600a may include different regions of varying intensity. For example, the patterned light beam 600a a first region 601, second region 603, and third region 605, with the second region having an intensity that may be substantially less than the intensity of the first and/or third regions 601, 605, respectively. The time taken for a particle to pass through the first 601, second 603, and third 605 regions is represented by $t_1$ 615, $t_2$ 617, and $t_3$ 619, respectively. An angle θ 607 defines a sloping of the diagonal second region 603 in this embodiment. The label '$x_0$' 609 represents the smallest distance a particle may pass through the first region 601 before reaching the second region 603. The light beam pattern 600a may be defined by a total distance (D) 611. A position of the particle in the y, or third, dimension 613, representing a transverse location of the particle in a particle path 612 may be obtained using the geometrical properties of the pattern 600a and time signals by $t_1$ 615, $t_2$ 617, and $t_3$ 619. The label 'x' 621 represents a side of a triangle, formed in the first region 601, by the transverse position y 613 and the angle θ 607. The term '$vt_1$' represents a mathematical expression of the distance traveled in the first region 601 by the particle in the particle path 612.

Using the geometrical configuration described above, it should be appreciated that the total time taken for a particle to pass through the pattern beam 600a may be represented by equation (1):

$$T = t_1 + t_2 + t_3 \quad (1)$$

The relationship between a total distance (D) and a total time (T) may be used to find a velocity (v) of the particle traveling in the particle path 612, as shown in equation (2):

$$v = \frac{D}{T} \quad (2)$$

Using the tangent relationship of the angle θ 607 with respect to the transverse position y 613 and x 621, equation (3) may be derived:

$$\frac{y}{x} = \tan(\theta) \quad (3)$$

Solving for x in equation (3) yields the following equation:

$$x = \frac{y}{\tan(\theta)} \quad (4)$$

Using the geometrical relationship between '$vt_1$' 623, $x_0$ 609, and x 621 shown in FIG. 6A, the following equation may be obtained:

$$x_0 + x = vt_1 \quad (5)$$

Since the value of the distance (D) 611 of the pattern 600a may be substantially small, it may be assumed that the velocity of the particle traveling the first region 601 is equal to the velocity of the particle traveling through the entire pattern. Thus, the value for the particle velocity (v) obtained in equation (2) may be substituted into equation (5) yielding:

$$x_0 + x = vt_1 = \frac{Dt_1}{T} \quad (6)$$

Substituting the value of x from equation (4) into equation (6) yields:

$$x_0 + \frac{y}{\tan(\theta)} = vt_1 = \frac{Dt_1}{T} \quad (7)$$

Finally, solving for the transverse particle position value (y) in equation (7) yields:

$$y = \left(\frac{Dt_1}{T} - x_0\right)\tan(\theta) \quad (8)$$

Thus, based on the measurements $t_1$ 615, $t_2$ 617, and $t_3$ 619, as well as knowledge of the total distance (D) 611, '$x_0$' 609, and the angle θ 607, the transverse particle position y 613 may be obtained.

FIG. 6B shows an alternative geometrical confirmation of the beam pattern 600b that may be used for finding the transverse particle position y 613. The beam pattern 600b comprises a majority of the geometrical relationships of the previous beam pattern 600a with a few differences. In beam pattern 600b, the label '$x_0$' 633 represents the smallest distance a particle may pass through the first region 601 before reaching a center 634 of the second region 603. The label 'x' 643 is the distance between the center 634 and an intersection center 635. The intersection center 635 may represent a location where the particle, traveling in the particle path 612, intersects with the center of the second region 603. The label '$vT_1$' is a mathematical expression representing the total distance traveled in the first region 601 through the center of the second region 603, with timing signal $T_1$ 639 representing the time of travel. The timing signal $T_2$ 641 represents the remaining time of travel, or the time of travel between the center of the second region 603 through the end of the third region 605. $T_2$ 641 may be obtained from a graph similar to the graph 527 shown in FIG. 5C (i.e., $T_2 = t_2/2$).

Using the mathematical relationships of equations (1)-(8), a value for the transverse particle position y 613 may be obtained for the configuration of pattern 600b:

$$y = \left(\frac{DT_1}{T} - x_0\right)\tan(\theta) \quad (9)$$

It should be appreciated that any other geometrical pattern configuration may be employed in the determination of the transverse particle position y 613 from timing measurements. Additionally, it should be appreciated that the light beam pattern need not have sharp edges or a binary intensity profile, as shown in FIGS. 6A and 6B. It is only required that the light beam pattern provides distinct timing signals for transverse particle paths separated by resolution distances of interest.

Figure 7:
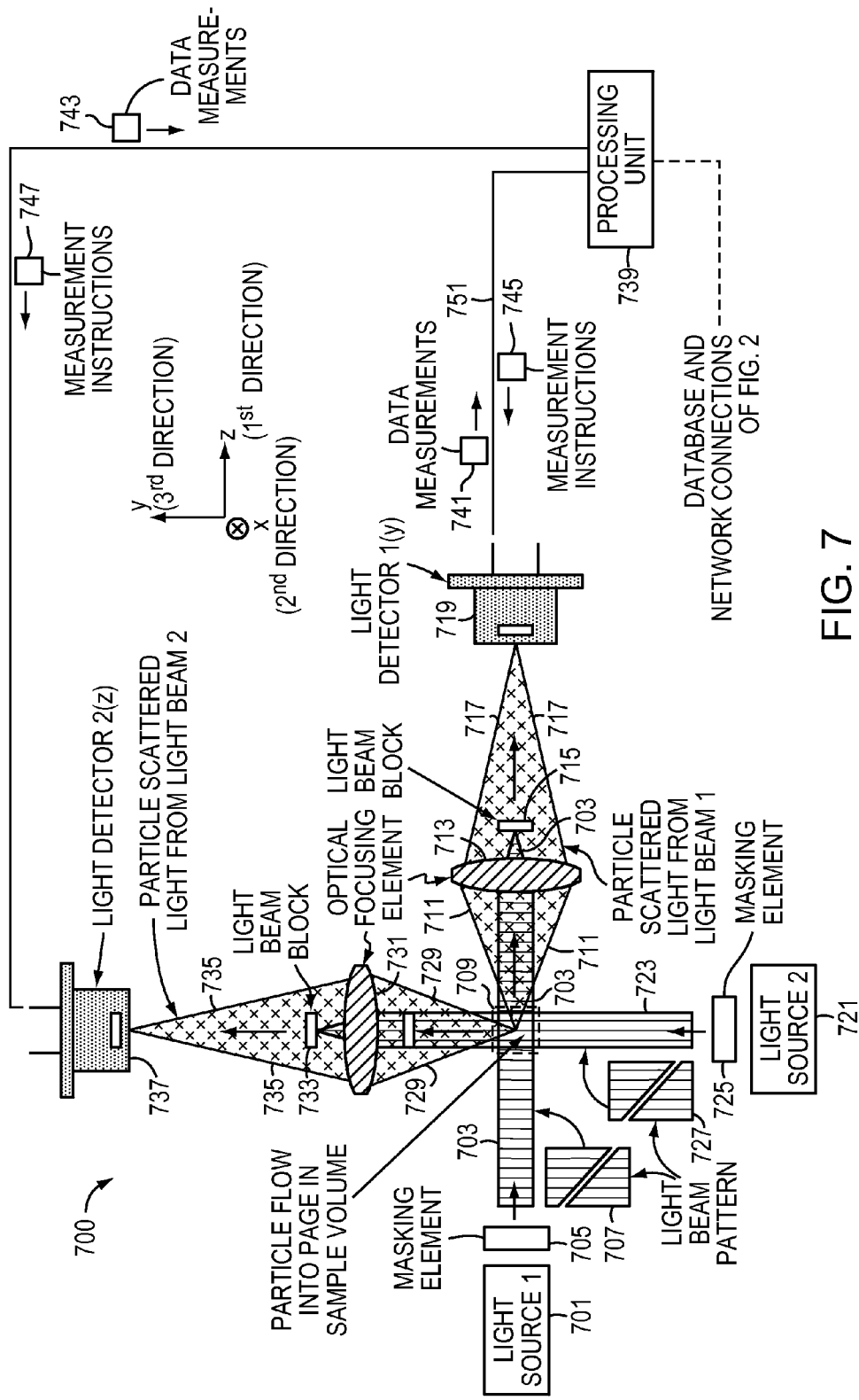
FIG. 7 is a schematic diagram of a patterned beam particle detection system for determining a position of a particle in two physical dimensions in an air flow, according to an embodiment of the present invention.
Figure 8:
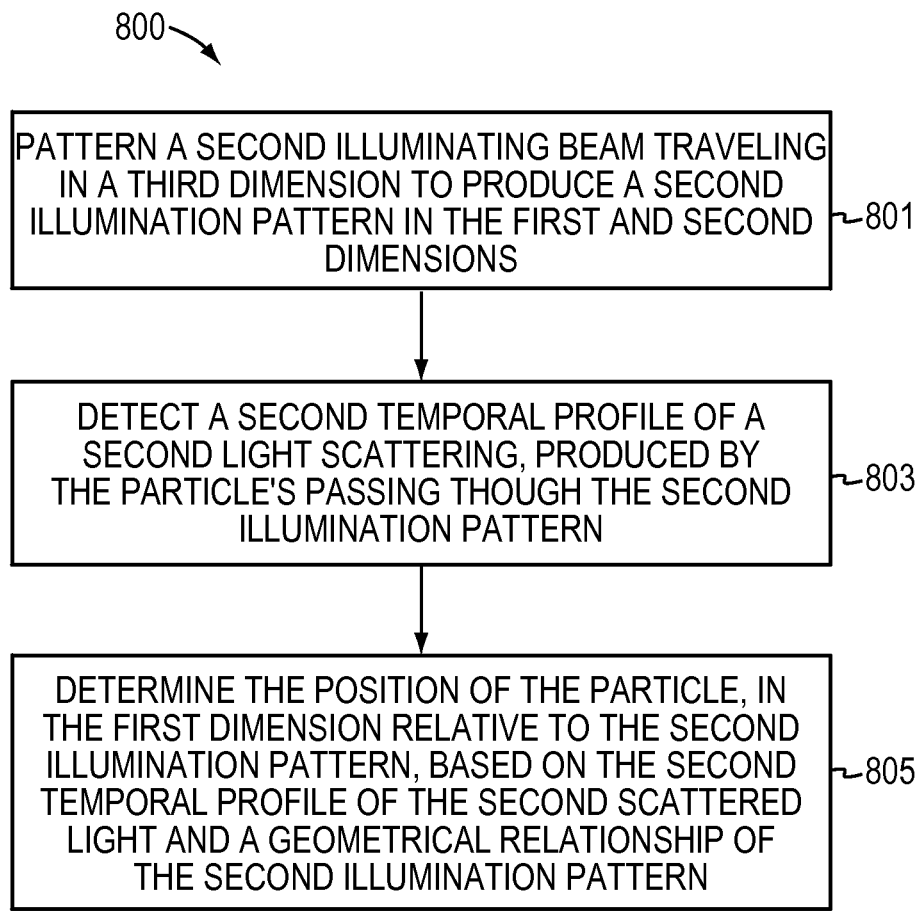
FIG. 8 is a flow diagram of an overview of operations of the detection system of FIG. 7.

FIG. 7 shows a depiction of a particle detection system 700 capable of producing two particle positions, one position in a transverse position (the y, or third, dimension) and a particle position in a longitudinal direction (the z, or first, dimension). FIG. 8 shows a flow diagram 800 of an overview of operations that may be taken by the detection system 700. It should be appreciated that the operations described in FIG. 3 are also performed in the detection system 700 of FIG. 7.

Referring to FIG. 7, the particle detection system 700 includes a light source 701 configured to produce a propagating light beam 703 in the z, or first, dimension in this example embodiment. The light source 701 may be coupled to a masking element 705, such that once the light source 701 illuminates the masking element 705, a light beam pattern 707 is produced in the propagating beam 703 in the x, or second, and y, or third, dimensions. The propagating beam 703 comprising the light pattern 707 may be configured to intersect a sample volume 709 through which a particle flow flows in the x, or second, dimension. As the particles in the sample volume 709 pass through the light beam pattern 707 of the propagating beam 703, a diverging scattered light 711 may be produced. Similar to the light scattering 211 of FIG. 2, the diverging light scattering 711 defines a temporal profile. The temporal profile has defined therein timing values indicative of the particle's position, in the sample volume 709, in the y, or third, dimension. The diverging scattered light 711 and the propagating beam 703 may be passed through an optical focusing element 713, resulting in a converging scattered light 717. The patterned beam 703 may be blocked by a light beam block 715 in order to prevent a first light detector 719 from receiving the beam 703, thus reducing the risk of detector saturation. The converging scattered light 717 may be focused onto the light detector 719.

The particle detection system 700 may also include a second light source 721 that may be configured to produce a propagating beam 723 in a y, or third, dimension. The light source 721 may be coupled to a masking element 725 in order to produce a light beam pattern 727 in the propagating beam 723 in the x, or second, and z, or first, dimensions (FIG. 8, 801). The propagating beam 723 may then be passed through the sample volume 709. Once the particles in the sample volume 709 pass through the light pattern 727 in the propagating beam 723, a diverging scattered light 729 may be produced. An optical focusing element 731 may be used to focus the pattern beam 723 onto a light beam block 733, thus preventing a saturation of a second light detector 737. The focusing element 731 may also be used to focus the diverging scattered light 729, resulting in converging scattered light 735. The converging scattered light 735 may define a temporal profile. The temporal profile may include timing values indicative of the particle's position, in the sample volume 709, in the z, or first, dimension. The converging scattered light 735 may be focused onto the second light detector 737 in order to detect the temporal profile provided by the scattering light 735 (FIG. 8, 803).

The light detectors 719 and 737 may be coupled to a processing unit 739. The light detectors 719 and 737 may be configured to send data measurements 741 and 743, respectively, to the processing unit 739. The processing unit 739 may be configured to determine the position of the particle in a y, or third, dimension in the sample volume 709 using the measurement data 741 provided by the first light detector 719. The processing unit 739 may also be configured to measure the position of the particle in the z, or first, dimension in the sample volume 709 using the measurement data 743 provided by the second light detector 737 (FIG. 8, 805). The processing unit 739 may be configured to send measurement instructions 745 and 747 to the light detectors 719 and 737, respectively. The instructions 745 and 747 may, for example, include on/off instructions. A data link 749 between the light detector 737 and the processing unit 739 and a data link 751 between the light detector 719 and the processing unit 739 may be any form of data transmission link known in the art. It should also be appreciated that the database and network connections of FIG. 2 may also be employed in the particle detection system 700 shown in FIG. 7.

It should also be appreciated that the masking element described in reference to FIGS. 2, 4, and 7 herein may, as an alternative to producing intensity variation, produce a beam pattern with portions of varying polarization.

Figure 9:
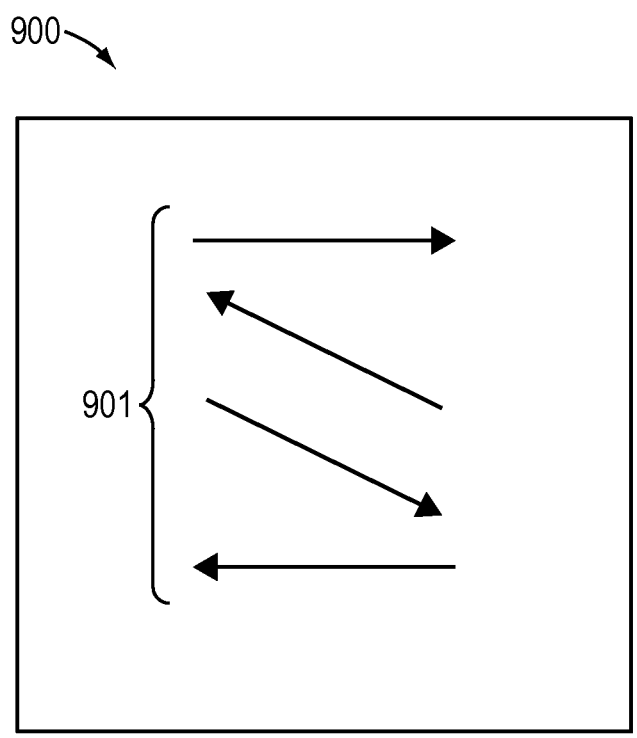
FIG. 9 is a depiction of an example of a polarization masking element, according to an embodiment of the present invention.

FIG. 9 shows a masking element 900 comprising a polarization inducing section 901 configured to produce a beam pattern comprising portions of varying polarization.

Figure 10:
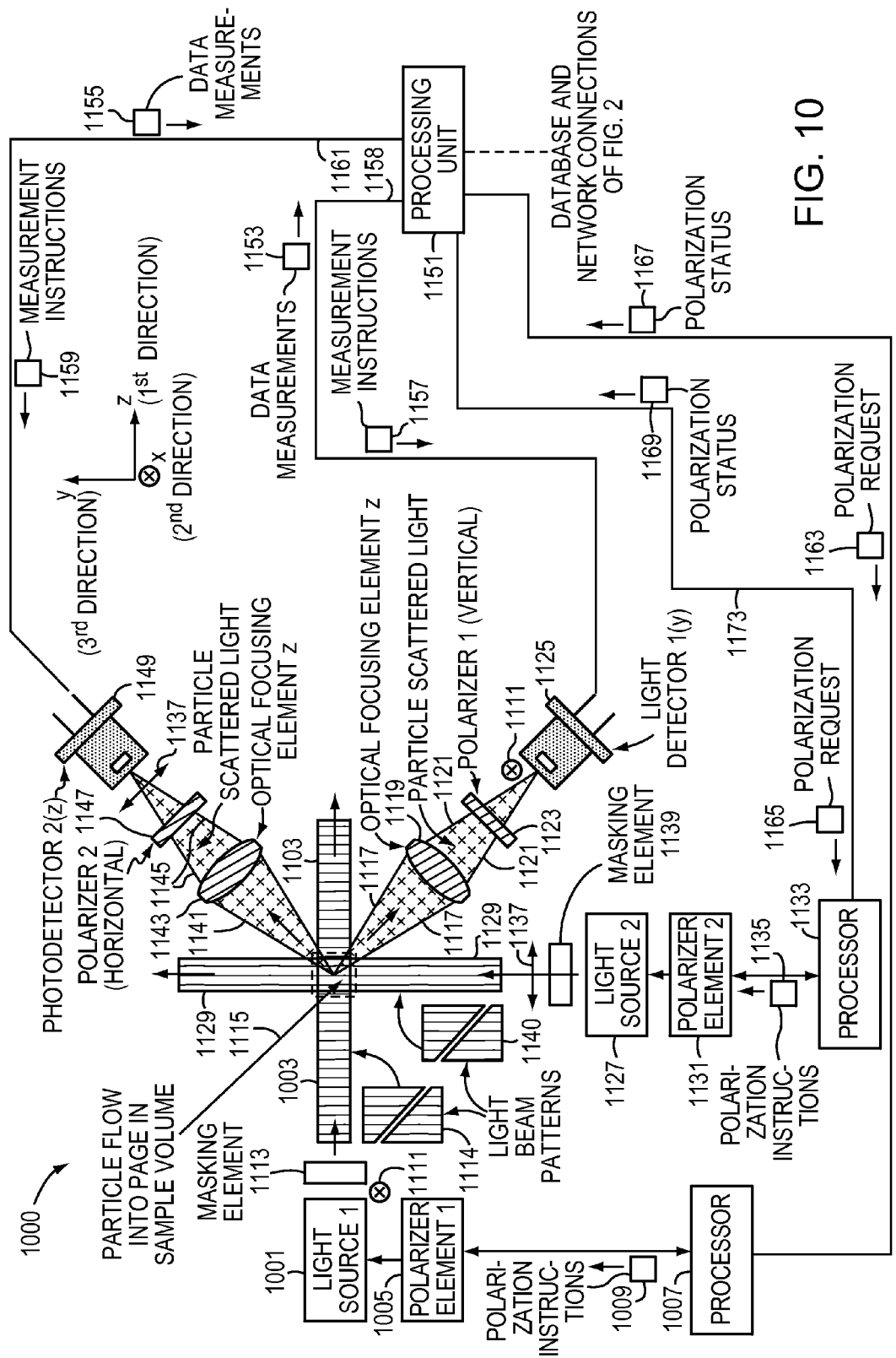
FIG. 10 is a schematic diagram of a patterned beam particle detection system featuring polarization coding for determining a position of a particle in two physical dimensions in an air flow, according to an embodiment of the present invention.

FIG. 10 is an example of a particle detection system 1000 capable of obtaining a particle position in a transverse, or y (third), dimension and a longitudinal direction, or z (second), dimension. The particle detection system 1000 may include a first light source 1001 configured to produce a propagating beam 1003 in the z, or first, dimension. The light source 1001 may be coupled to a polarizing element 1005. The polarizing element 1005 may be coupled to a first polarization processor 1007. The first polarization processor 1007 may provide polarization instructions 1009 to the polarizing element 1005. The polarizing element 1005 may induce a first polarization 1111 in the propagating beam 1003. A masking element 1113 may also be coupled to the light source 1001, in order to produce a light beam pattern 1114, in the x, or second, and y, or third, dimensions, in the propagating beam 1003. The propagating beam 1003 may be configured to pass through a sample volume 1115, comprising a particle flow in an x, or second, dimension.

As a result of the particles in the sample volume 1115 passing through the light beam pattern 1114 of the propagating beam 1003, a diverging scattered light 1117 is produced. The diverging scattering light 1117 may define a temporal profile. The temporal profile may be used to determine timing signals that are, in turn, used to determine a particle location in a y, or third, dimension. An optical focusing element 1119 may be configured to focus the diverging scattering light 1117 resulting in a converging scattering light 1121. The converging scattering light 1121 may be configured to pass through a first polarizer 1123 resulting in a filtration of the converging scattering light 1121, thus allowing only light having the first polarization 1111 to be passed through and focused on a first light detector 1125. Since the scattered light is focused off-axis with respect to the propagating beam 1003, a beam block is not needed in this configuration.

The particle detection system 1000 may also include a second light source 1127 configured to produce a propagating beam 1129 in a y, or third, dimension. The light source 1127 may be coupled to a second polarizing element 1131. The second polarizing element 1131 may be coupled to a second polarization processor 1133. The second polarization processor 1133 may provide polarization instructions 1135 to the second polarizing element 1131. The polarization instructions 1135 may be used by the second light source 1127 to produce a second polarization 1137 in the propagating beam 1129. A masking element 1139 may be coupled to the light source 1127 in order to produce a second light beam pattern 1140. The propagating beam 1129, comprising the light beam pattern 1140 and the second polarization 1137, may be configured to pass through the sample volume 1115.

As the particles in the sample volume 1115 pass through the light beam pattern 1140 a diverging scattering light 1141 may be produced. A second optical focusing element 1143 may be configured to focus the diverging scattering light 1141, resulting in a converging scattering light 1145. The converging scattering light 1145 may be configured to pass through a second polarizer 1147, thus resulting in the filtering of the converging scattering light 1145 and, therefore, allowing only light featuring the second polarization 1137 to pass through. The filtered light is then focused onto a second light detector 1149. Since the scattered light is focused off-axis with respect to the propagating beam 1129, a beam block is not needed in this configuration.

The particle detection system 1000 may also employ a processing unit 1151 coupled to the first light detector 1125 and the second light detector 1149. The first and second light detectors 1125 and 1149, respectively, may provide data measurements 1153 and 1155, respectively, to the processing unit 1151. The processing unit 1151 may be configured to determine a particle position in the y, or third, and z, or first, dimensions using the supplied data measurements 1153 and 1155, respectively. The determined particle positions may be based on timing signals obtained from the respective temporal profiles. The processing unit 1151 may also provide measurement instructions 1157 and 1159 to the first and second light detectors 1125 and 1149, respectively via communications links 1158, 1161. The instructions 1157 and 1159 may comprise on/off instructions.

The processing unit 1151 may also be coupled to the first and second polarization processing units 1007 and 1133, of the first and second light sources 1001 and 1127, respectively. The processing unit 1151 may provide a polarization request 1163 and 1165 to the first and second polarization processing units of the first and second light sources, respectively. The polarization requests 1163 and 1165 provide polarization settings for the light sources 1001 and 1127, respectively. The first and second polarization processing units of the first and second light source 1007 and 1133, respectively, may also provide a polarization status 1167 and 1169, respectively, to the processing unit 1151. The polarization status 1167 and 1169 may provide a current polarization setting of the polarizing elements 1005 and 1131, respectively. It should be appreciated that the database and networking connections shown in FIG. 2 may also be implemented in the particle detection system 1000 of FIG. 10.

Figure 11:
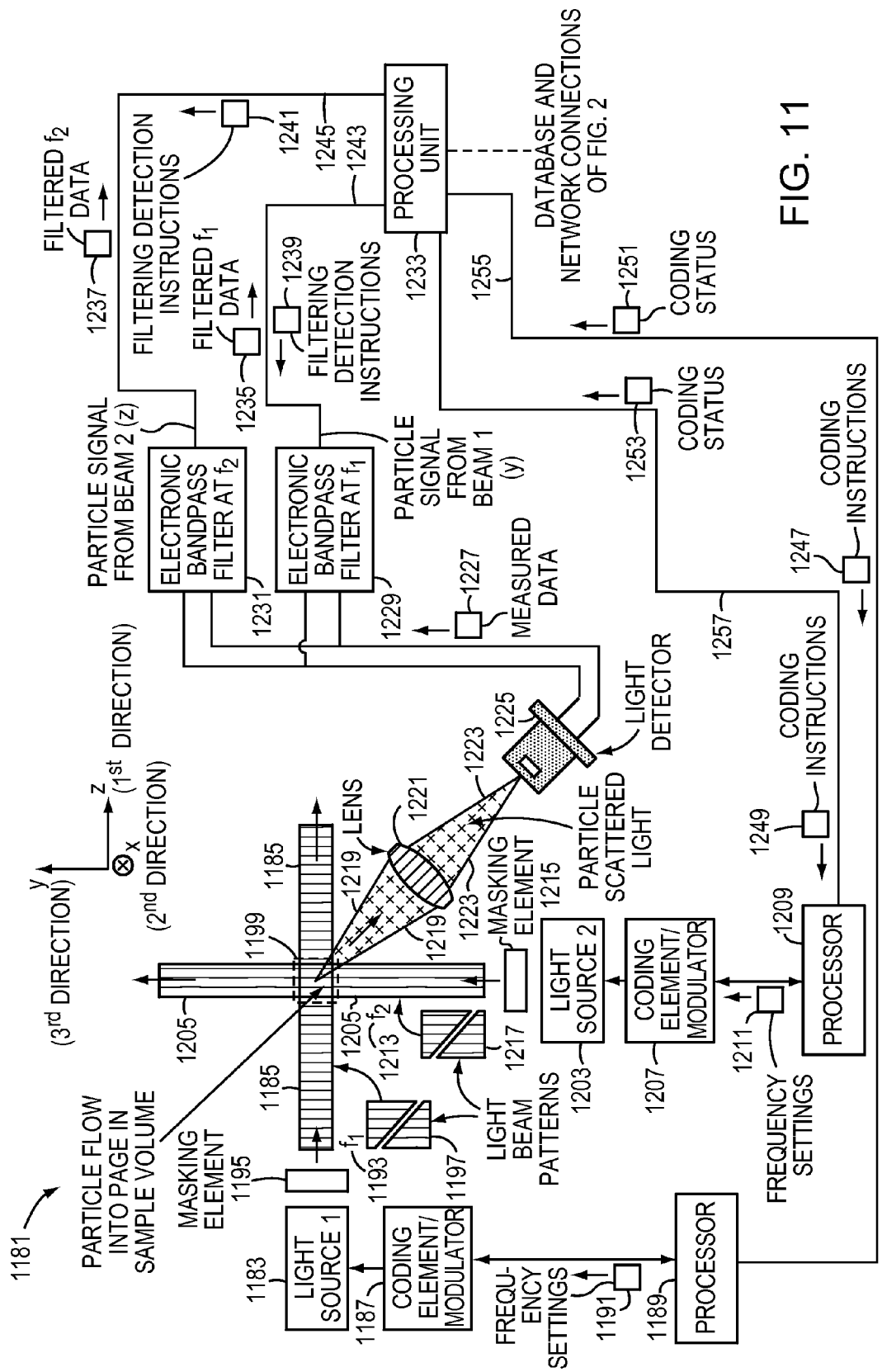
FIG. 11 is a schematic diagram of a patterned beam particle detection system featuring modulation coding for determining a position of a particle in two physical dimensions in an air flow, according to an embodiment of the present invention.

FIG. 11 illustrates another configuration of a particle detection system 1181 which may provide a particle position in a transverse (y), or third, dimension, and in a longitudinal (z), or first, dimension. In contrast to the detection systems shown in FIGS. 7 and 10, the detection system 1181 may be configured to use a single light detector 1225. The detection system 1181 may employ a first light source 1183 configured to provide a propagating beam 1185 in the z, or first, dimension. A coding element 1187 may be coupled to the first light source 1183. In the configuration shown in FIG. 11, the coding element 1187 may be a modulator configured to provide temporal modulation, resulting in a frequency setting ($f_1$) induced in the first light source 1183. Thus, the illumination of the beam 1185 includes a first frequency 1193. A processor 1189 may be coupled to the first coding element 1187 in order to provide frequency settings 1191. A masking element 1195 may be coupled to the first light source 1183 in order to provide a light beam pattern 1197 in the x, or second, and y, or third, dimensions, in the propagating beam 1185. The propagating beam 1185 comprising the light beam pattern 1197, and illuminating at a first frequency 1193 may be configured to pass through a sample volume 1199 comprising a flow of particles in an x, or second, dimension.

The particle detection system 1181 may also comprise a second light source 1203 configured to provide an illuminating beam 1205 in the y, or third, dimension. A second coding element 1207 may be coupled to the second light source 1203 in order to provide a second frequency ($f_2$) 1213 to the illuminating beam 1205. A second modulation processor 1209 may be coupled to the second coding element 1207 in order to provide frequency setting 1211, providing a value of the second frequency 1213. A masking element 1215 may be coupled to the second light source 1203 in order to provide a second light beam pattern 1217 in a z, or first, and x, or second, dimensions. The propagating beam 1205, comprising the light beam pattern 1217 and illuminating at a second frequency 1213, may be configured to pass through the sample volume 1199 with the particle flow in an x, or second, dimension.

As the particles in the sample volume 1199 pass through the light beam patterns 1197 and 1217 of the propagating beams 1185 and 1205, respectively, a combined diverging scattering light 1219 is produced. The diverging scattering light 1219 defines a temporal profile comprising position information about the particles in the z, or first, and y, or third, dimensions, in the sample volume 1199. The light scattering produced by the first light beam pattern 1197 may produce information indicative of a particle position in the y, or third, dimension. The light scattering produced by the second light beam pattern 1215 may produce information indicative of a particle position in the z, or first, dimension.

An optical focusing element 1221 may be configured to focus the diverging scattering light 1219, resulting in a converging scattering light 1223. The converging scattering light 1223 is focused onto a light detector 1225. First and second bandpass filters 1229 and 1231, respectively, may be coupled to the light detector 1225. In this example embodiment, the light detector 1225 sends measured data 1227 to the first and second bandpass filters 1229 and 1231, respectively. The first bandpass filter 1229 may be configured to filter out all data in the measured signal 1227 not having information of the first frequency 1193. Similarly, the second bandpass filter 1231 may be configured to filter out all data in the measured signal 1227 not having information of a second frequency 1213.

A processing unit 1233 may be coupled to the first and second filters 1229 and 1231, respectively. In this example embodiment, the first and second bandpass filters 1229 and 1231, respectively, are configured to provide filtered measurement data 1235 and 1237, respectively, to the processing unit 1233. The processing unit 1233 may be configured to determine a particle position in the y, or third, and z, or first, dimensions using the filtered data 1235 and 1237, respectively. The determined particle positions may be based on timing signals obtained from the temporal profile. The processing unit 1233 may be configured to provide filtering or detection instructions 1239 and 1241 to the first and second filters 1229 and 1231, respectively. The filtering instructions 1239 and 1241 may include on/off commands as well as frequency detection settings.

The processing unit 1233 may also be coupled to the first and second modulation processors 1189, 1209 of the first and second light sources 1183 and 1203, respectively. The processing unit 1233 may send coding instructions 1247 and 1249 to the first and second modulation processors 1189 and 1209, respectively. The coding instructions 1247 and 1249 may contain frequency settings used to program the first and second coding elements 1187 and 1207, respectively. The first and second modulation processors 1189 and 1209 may be configured to send a coding status 1251 and 1253, respectively, to the processing unit 1233. The coding status 1251 and 1253 may comprise information of a current frequency setting. It should be appreciated that the particle detection system 1181 may also employ the database and network configurations shown in FIG. 2.

Figure 12A:
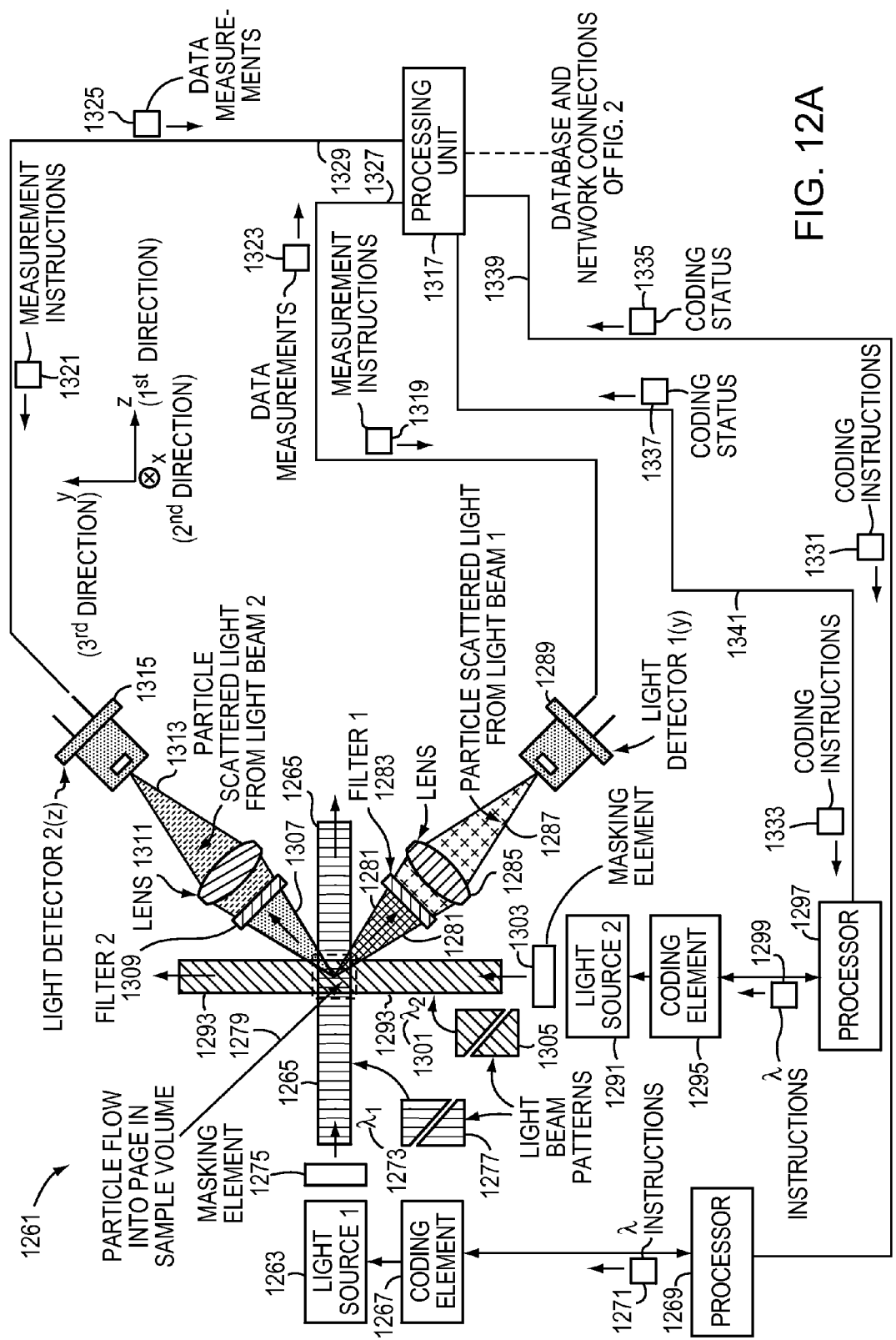
FIGS. 12A and 12B are schematic diagrams of a patterned beam particle detection system featuring illumination wavelength coding to determine a position of a particle in two physical dimensions in an air flow, according to an embodiment of the present invention.

FIG. 12A illustrates a particle detection system 1261 capable of determining a particle position in a transverse (y), or third, dimension, and a longitudinal (z), or first, dimension. The particle detection system 1261 may employ a first light source 1263 configured to provide a propagating beam 1265 in the z, or first, dimension. A first coding element 1267 may be coupled to the first light source 1263. A first coding processor 1269 may be coupled to the first coding element 1267 in order to provide coding instructions 1271. In the example shown in FIG. 12A, the coding instructions may be wavelength instructions used for selecting an illumination wavelength of the first light source 1263. A masking element 1275 may be coupled to the first light source 1263 in order to provide a light beam pattern 1277 in the y, or third, and x, or second, dimensions. The propagating beam 1265, comprising the selected wavelength 1273 and light beam pattern 1277, may be configured to pass through a particle flow in a sample volume 1279. As the particles in the sample volume 1279 pass through the light beam pattern 1277, a diverging scattering light 1281 is produced. The diverging scattering light 1281 may be configured to pass through a first filter 1283 allowing light of only the selected wavelength 1273 to pass through. An optical focusing element 1285 may be configured to focus the diverging scattering light 1281 resulting in converging scattering light 1287 focused onto a light detector 1289.

The particle light detection system 1261 may also employ a second light source 1291 configured to provide a propagating beam 1293 in the y, or third, dimension. A second coding element 1295 may be coupled to the second light source 1291. A second coding processor 1297 may be coupled to the second coding element 1295 in order to provide coding instructions 1299. The coding instructions 1299 may include wavelength illumination instructions used in selecting a second wavelength 1301 for an illumination produced by the second light source 1291. A masking element 1303 may be coupled to the second light source 1291 in order to produce a second light beam pattern 1305 in the z, or first, and x, or second, dimensions. The propagating beam 1293, including the second selected wavelength 1301 and the second light beam pattern 1305, may be configured to pass through the sample volume 1279. As the particles in the sample volume 1279 pass through the second light beam pattern 1305, a second diverging scattering light 1307 may be produced. A second filter 1309 may be configured to filter the diverging scattering light 1307, such that only light comprising the second selected wavelength 1301 may pass. A second optical focusing element 1311 may be configured to focus the diverging scattering light 1307 resulting in a converging scattering light 1313 being focused on a second light detector 1315.

The particle detection system 1261 may also comprise a processing unit 1317 coupled to the first and second light detectors 1289 and 1315, respectively. The processing unit 1317 may be configured to provide measurement instructions 1319 and 1325 to the first and second particle detectors 1289 and 1315, respectively. The measurement instructions 1319 and 1325 may provide on/off commands or wavelength detection settings. The first and second light detector 1289 and 1315 may be configured to provide data measurements 1323 and 1325, respectively, to the processing unit 1317. The processing unit 1317 may be configured to determine a particle position in the y, or third, and z, or first, dimensions using the supplied data measurements 1323 and 1325, respectively. The determined particle positions may be based on timing signals obtained from the respective temporal profiles. The processing unit 1317 may also be coupled to the coding processors of the first and second light sources 1269 and 1297, respectively. The processing unit 1317 may provide coding instructions 1331 and 1333 to the first and second coding processors 1269 and 1297, respectively. The first and second coding processors 1269 and 1297 may provide a coding status 1335 and 1337, respectively, to the processing unit 1317. It should be appreciated that the database and network connections of FIG. 2 may also be incorporated into the particle detection system 1261. It should also be appreciated that data transmission links 1339, 1341, 1327, and 1329 may comprise any data transmission link known in the art.

Figure 12B:
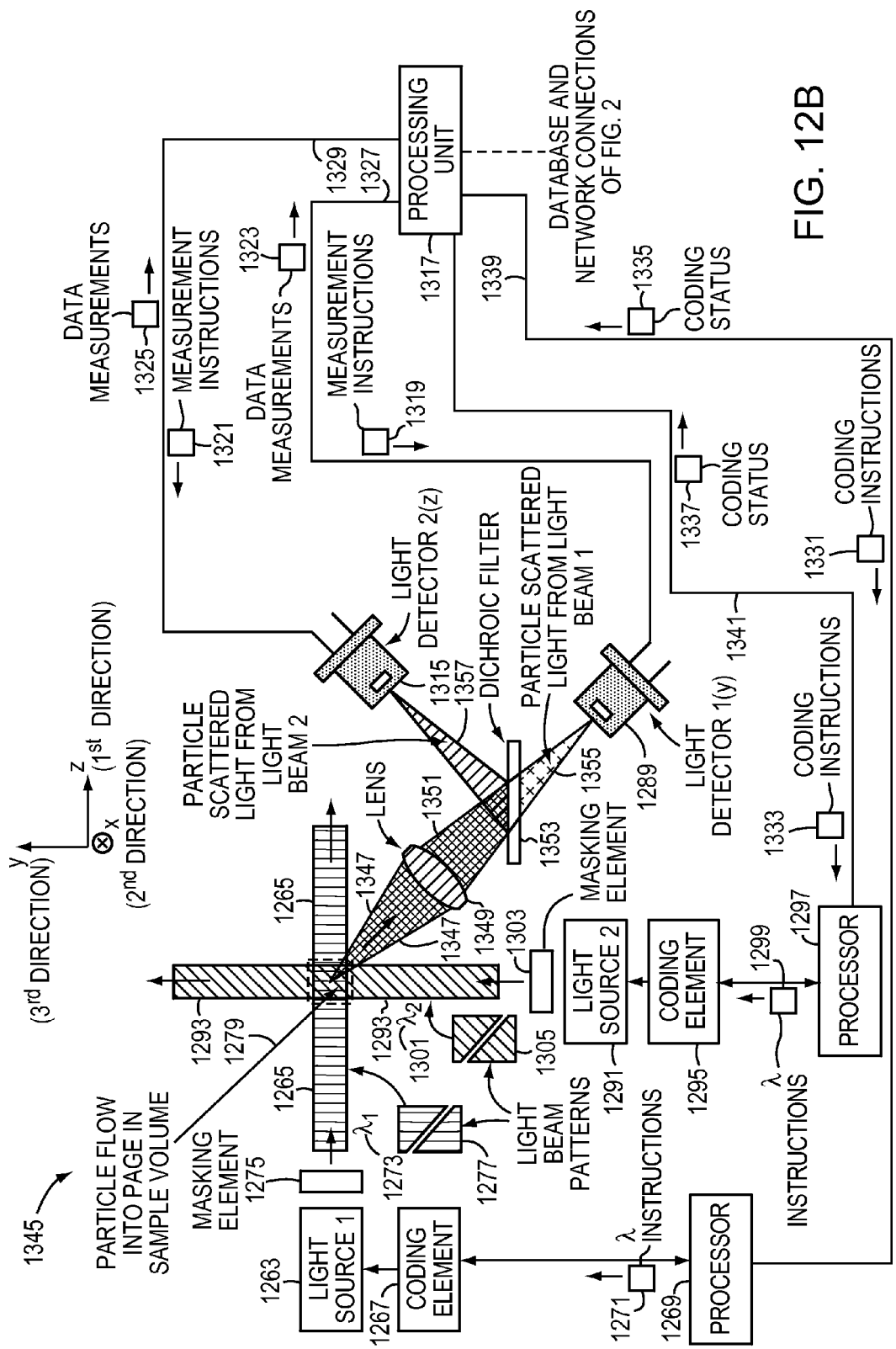

FIG. 12B provides an alternative configuration 1345 of the particle detection system shown in FIG. 12A. The alternative configuration 1345 provides a more compact system. Instead of employing two filters, as shown in the particle system 1261, a single dichroic filter 1353 may be used. Thus, as the particles in the sample volume 1279 pass through the light beam patterns 1277 and 1303, a combined diverging scattering light 1347 is produced. The combined scattering light 1347 may define a temporal profile indicative of a particle position in the z, or first, dimension, and y, or third, dimension. The temporal profile may provide timing signals indicative of particle position to be used by the processing unit 1317.

An optical focusing element 1349 may be used to focus the combined diverging scattering light 1347 in order to produce a converging scattering light 1351. Upon passing the dichroic filter 1353, the converging scattering light 1351 may be decomposed into a first converging scattering light 1355 of the first selected wavelength 1273 and a second converging scattering light 1357 of the second selected wavelength 1301. The first filtered scattering light 1355 may be focused onto a first light detector 1289 and the second scattering light 1357 may be focused onto the second light detector 1315.

Figure 13A:
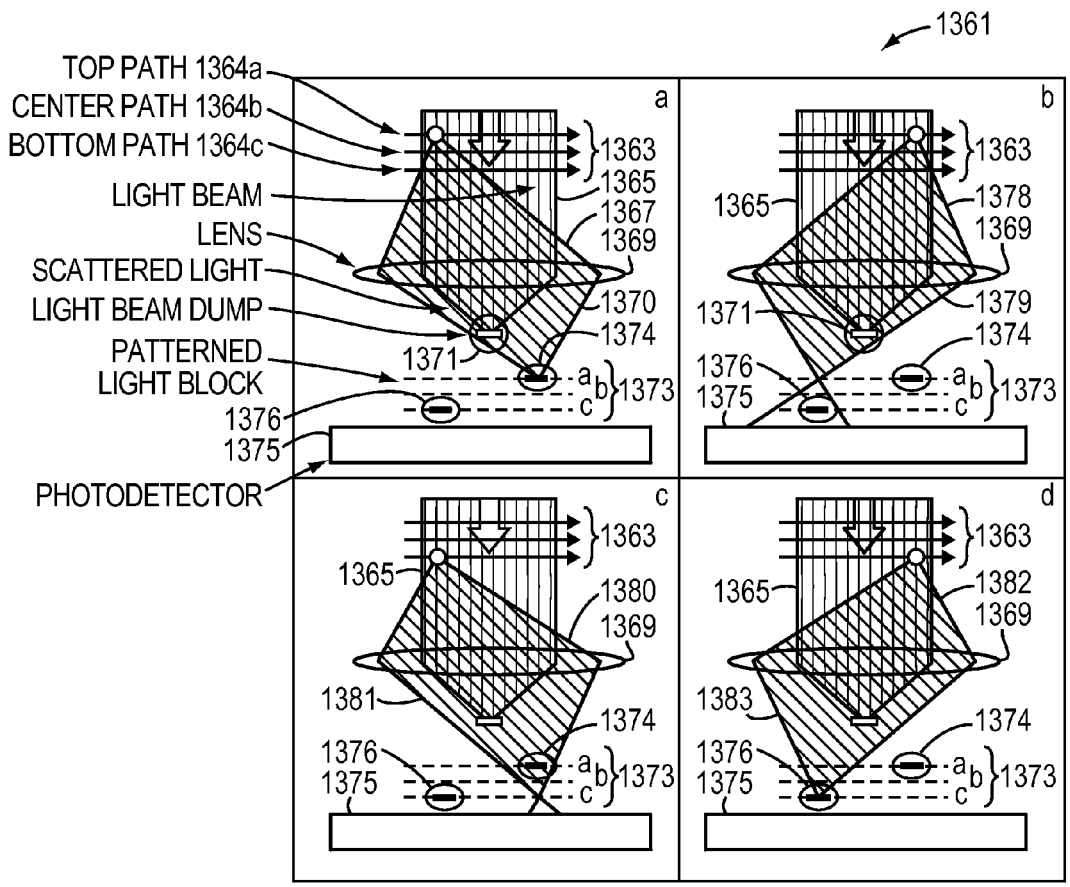
FIGS. 13A and 13B are schematic diagrams of an optical block particle detection system for determining a position of a particle in an air flow, and an example measurement signal, respectively, according to an embodiment of the present invention.
Figure 14:
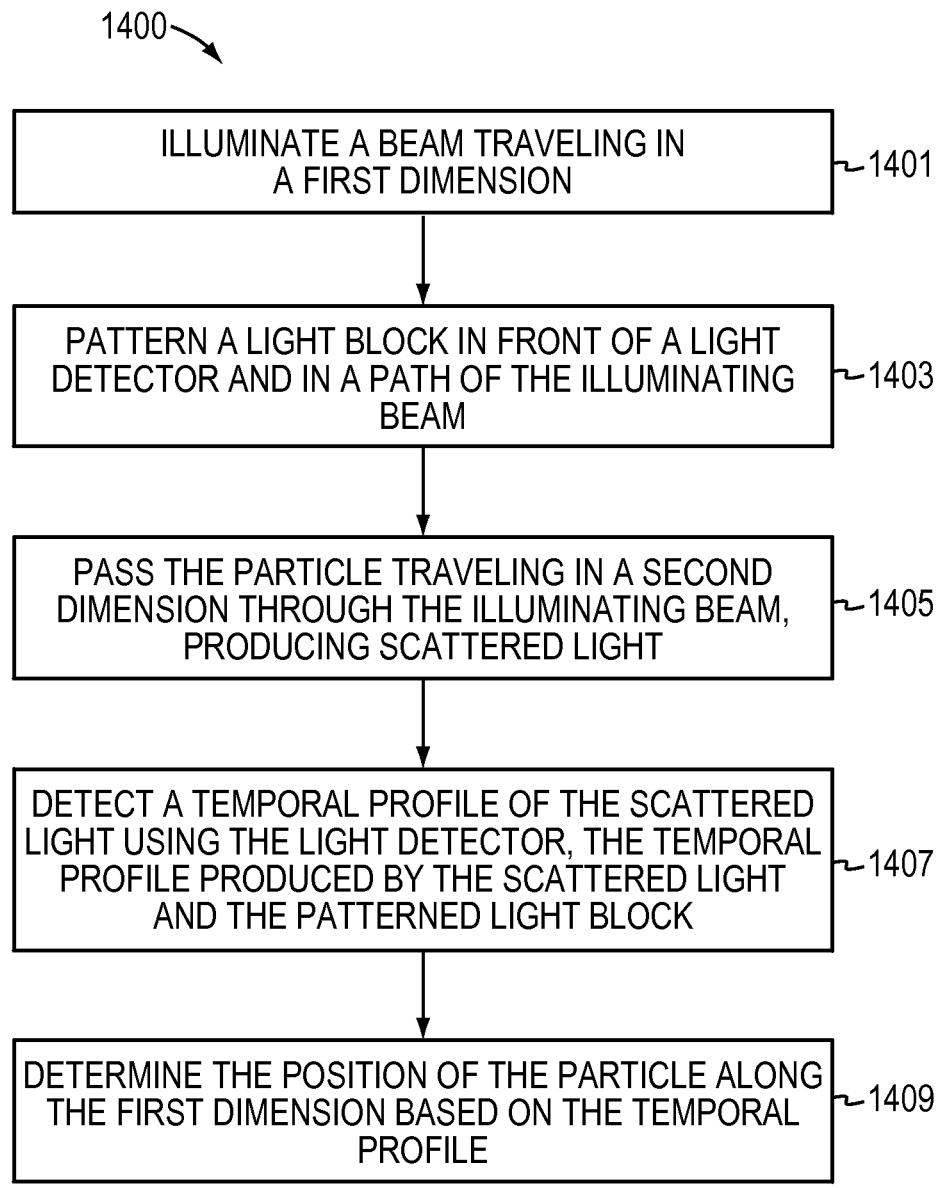
FIG. 14 is a flow diagram of an overview of operations of the detection system of FIGS. 13A and 13B.

FIG. 13A provides illustrations of a particle detection system 1361 in examples a-d that may provide a longitudinal particle position in a z, or first, dimension. FIG. 14 provides a flow diagram describing an overview the operations taken by the particle detection system 1361. Referring to FIGS. 13A and 14, in the first particle detection system 1361a, an illumination beam 1365 may be configured to travel in the z, or first, dimension (FIG. 14, 1401). The illumination beam 1365 may further be configured to intersect a sample volume 1363 through which particles traveling in an x, or second, dimension travel. The particles may travel, for example, in a top path 1364a, center path 1364b, or bottom path 1364c. The top, center and bottom paths represent different positions of the particle in the z, or first, dimension.

As the particle travels in the x, or second, dimension and passes through the illumination beam 1365, a diverging scattering light 1367 may be produced (FIG. 14, 1405). The diverging scattering light 1367 may define a temporal profile that may, by the scattering, further include information indicative of the particle position in the z, or first, dimension. An optical focusing element 1369 may be configured to focus the diverging scattering light 1367, resulting in a converging scattering light 1370. A light blocker 1371 may be used to block the illumination beam 1365, thus preventing a photodetector 1375 from "seeing" the illumination beam 1365, and, therefore, preventing detector saturation. The converging scattering light 1370 may be focused onto a patterned optical block 1373a, 1373b, 1373c placed in front of the detector 1375 (FIG. 14, 403). The optical block 1373a-c may include three sections, for example, a top section 1373a, center section 1373b, and bottom section 1373c. The top and bottom sections of the optical block 1373a, 1373c may use blocking sections 1374 and 1376, respectively, which may partially or completely block the scattering light 1370 from reaching the photodectector 1375 (FIG. 14, 1407). Measuring a relative amount of light blocked by the blocking patterns 1374 and 1376, with respect to an amount of unblocked light, may provide information about where the particle is traveling in the z, or first, dimension (FIG. 14, 1409).

Figure 13B:
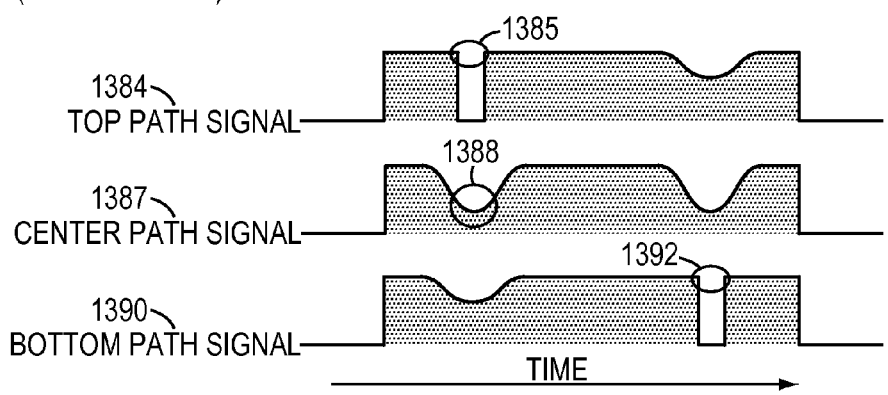

FIG. 13B provides an example of measured signals which may be obtained using the particle detection system 1361. The top path signal 1384 provides an example signal that may be obtained from a particle traveling along the top path 1364a, as shown in the system in FIG. 13A. As shown in FIG. 13A, a particle traveling along the top path 1363a results in a converging scattering light 1370 that is focused on the top layer of the optical block 1373a, while the light scattering may be transmitted through the center and bottom layers of the optical beam block 1373b and 1373c, respectively. Therefore, the top path signal 1384 includes a "clear blocking" section 1385, indicating that the particle has traveled along the top path 1364a. If the particle has traveled only along the top path 1364a, then only the top path signal 1384 may includes the clear blocking portion 1385. As illustrated in FIG. 13B, the center and bottom path signals 1387 and 1390, respectively, do not have a clear blocking section 1385 if the particle is traveling along the top path 1364a.

As also illustrated in FIG. 13A, if a particle is traveling along the bottom path 1364c of the sample volume 1363, then only the bottom path signal 1390 includes a clear blocking portion 1392. If the particle is traveling along the center path 1364b of the sample volume 1363, then neither the top nor bottom path signal 1384, 1390 has a blocking portion. Based on which signal 1384, 1387, 1390, a determination can be made as to which path 1384a-c the particle traveled.

As is shown in FIG. 13B, a particle traveling in the top portion, regardless of its position in the x, or second, dimension, may produce scattered light that only focuses on the top portion of the optical block 1373a, thus being "transparent" to the middle and bottom portions of the optical block 1373b and 1373c, respectively. Similarly, as seen in the particle detection systems 1361, example c, a particle traveling in the bottom path 1364c of the sample volume 1363 may produce scattering light 1381 that may only be focused on the bottom layer of the optical block 1373c. Therefore, the produced scattered light 1380 may be capable of being transmitted through the top and middle layers of the optical block 1373a and 1373b, respectively. As seen from the optical particle system 1361, example d, the particle traveling in the bottom path, regardless of its position in the x, or second, dimension, is only focused on the bottom layer of the optical beam block 1376.

Figure 15:
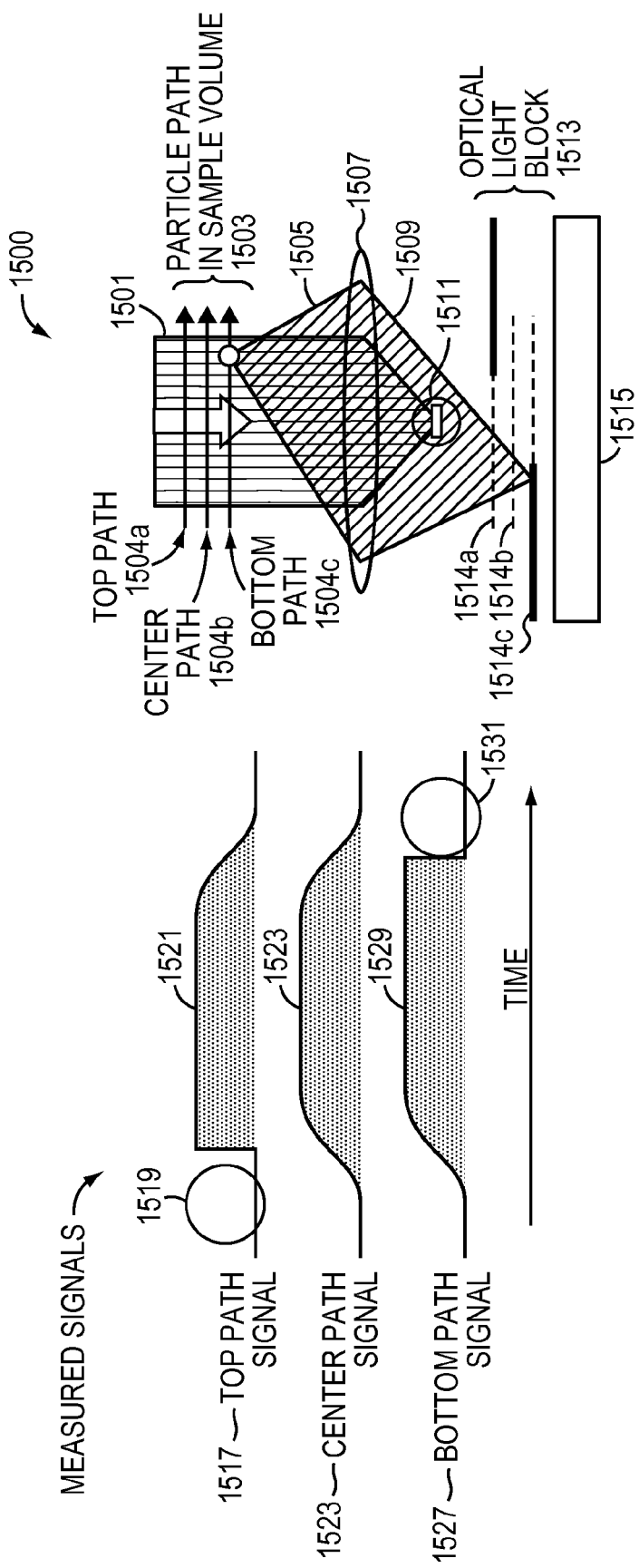
FIGS. 15A and 15B are a schematic diagram of an optical block particle detection system for determining a position of a particle in an air flow and example measurement signals, respectively, according to an embodiment of the present invention.

FIG. 15A shows a particle detection system similar to that of FIG. 13A, with the particle detection system in FIG. 15A employing a pattern light block 1513 with an alternative blocking pattern. The blocking pattern of optical block 1513 includes blocking edges, rather than the blocking regions of optical block 1373a-c of FIG. 13A. FIG. 15B provides example measurement signals which may be obtained from the particle detection system of FIG. 15A through use of the alternative blocking pattern of the optical block 1513. A particle traveling in the top path 1504a of the particle path 1503 may only be focused on a top portion 1514a of the optical block 1513. The resulting signal 1517 may comprise a completely blocked portion 1519 of a first portion of the obtained signal and an unblocked portion 1521 in a second portion of the signal 1517 indicative of the particle traveling in the top path 1504a. A particle traveling in the bottom path 1504c of the particle path 1503 may only be focused on the bottom portion 1514c of the optical block 1513. The resulting signal 1527 may represent an unblocked region 1529 in a first portion of the signal and a blocked region 1531 in a second portion of the signal. Finally, a particle traveling in the center path 1504b may only be focused in the center portion 1514b of the optical block 1513. The resulting signal 1523 may not comprise any portions indicative of a blocked signal, but only a portion representing an unblocked signal 1523.

Figure 16:
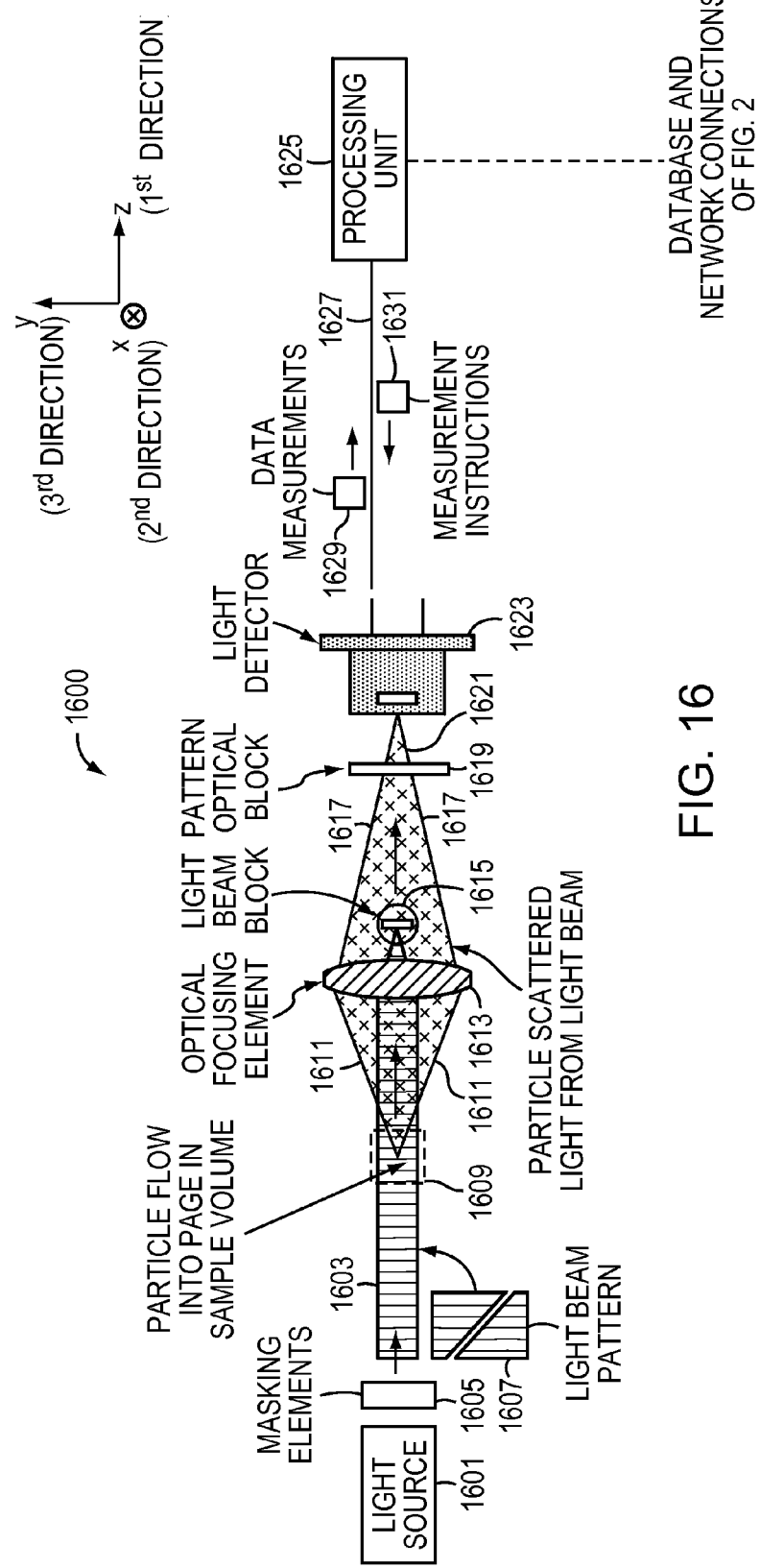
FIG. 16 is a schematic diagram of an optical block and patterned beam particle detection system for determining two positions of a particle in an air flow, according to an embodiment of the present invention.

FIG. 16 provides an example of a particle detection system 1600 capable of providing two particle positions in a longitudinal (z), or first, dimension, and a transverse (y), or third, dimension. The particle detection system 1600 may include a light source 1601 configured to provide a propagating beam 1603 propagating in the z, or first, dimension. A masking element 1605 may be coupled to the light source 1601 and may be configured to produce a light beam pattern 1607 in an x, or second, and y, or third, dimension, in the propagating beam 1603. As the propagating beam 1603, defining the light pattern 1607, is passed through a sample volume 1609 comprising particles, the particles passing through the light beam pattern 1607 may produce diverging scattering light 1611. An optical focusing element 1613 may be used to focus the diverging scattering light 1611, therefore producing converging scattering light 1617. An optical blocker 1615 may be used to block the illuminating beam 1603, thus preventing the light detector 1625 from receiving light from the illuminating beam 1603 and becoming saturated. The converging scattering light 1615 may be configured to pass through an optical beam block 1619. Upon passing through the optical beam block 1619, a partially blocked scattered light 1621 may be configured to be detected by the light detector 1623.

Figure 17:
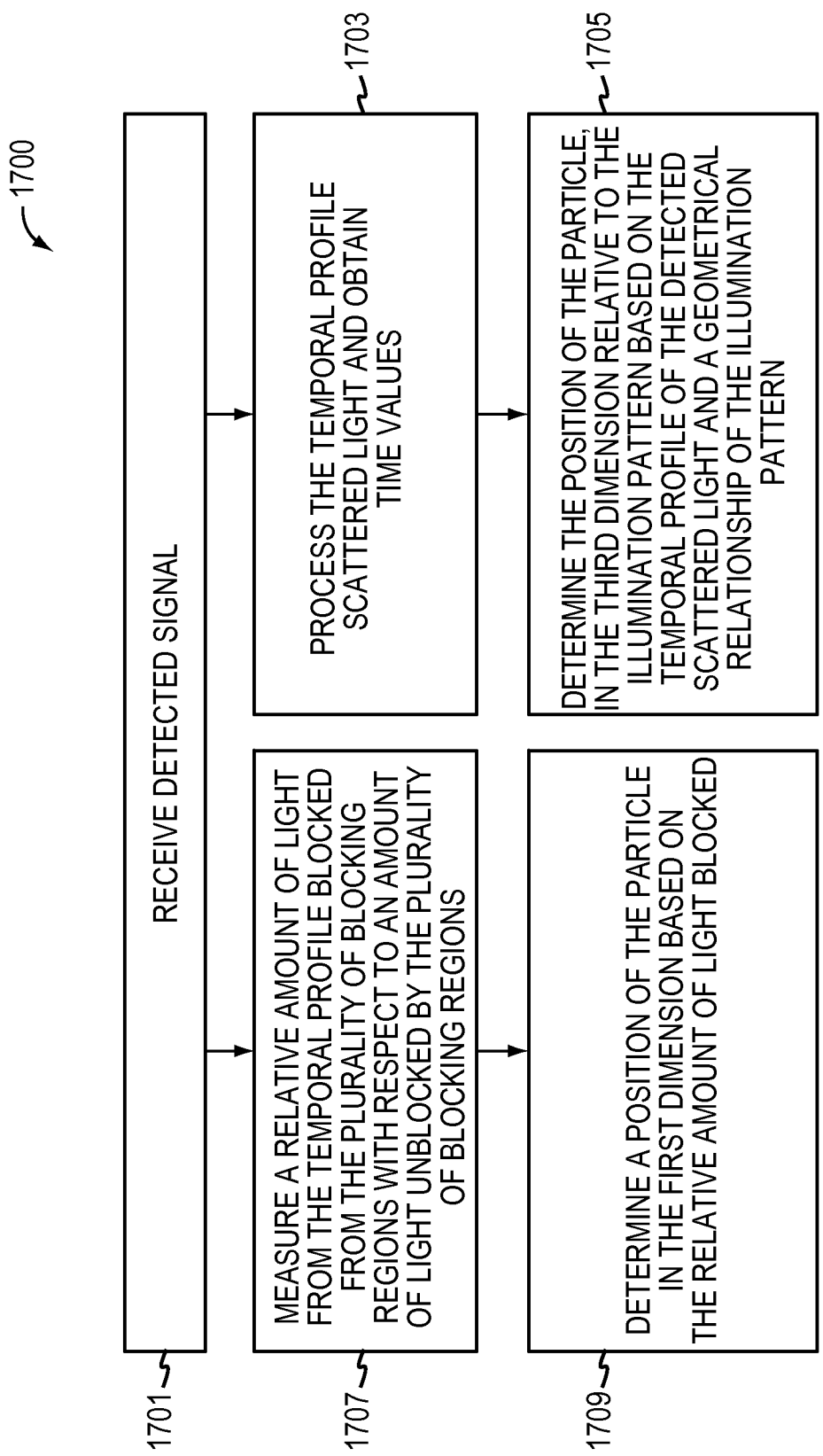
FIG. 17 is a flow diagram of an overview of operations of the detection system of FIG. 16.

FIG. 17 is a depiction of a flow diagram 1700 of an overview of the operations that may be taken by a processing unit 1625. The processing unit 1625 may be coupled to the light detector 1623. The light detector 1623 may provide data measurements 1629 to the processing unit 1625 (1701). The processing unit 1625 may provide measurement instructions 1631, which may comprise on/off directions, to the light detector 1623.

Using the temporal profile, the processing unit 1625 may process the profile in order to obtain multiple timing values, similar to the timing signals discussed in relation to FIGS. 5B, 5C, 6A, and 6B (1703). The processing unit 1625 may further be configured to determine a position of the particle in a transverse (y), or third, dimension using the timing values obtained from the temporal profile (1705).

Using blocking information obtained from the optical block 1619, the processing unit 1625 may be configured to measure a relative amount of light blocked from the blocking regions of the light block, with respect to an amount of light unblocked by the plurality of blocking regions (1707). The processing unit may be further configured to determine a position of the particle in the longitudinal (z), or first, dimension, based on the relative amount of light blocked (1709). It should be appreciated that the processing unit 1625 may comprise the database and network configurations shown in FIG. 2.

Figure 18:
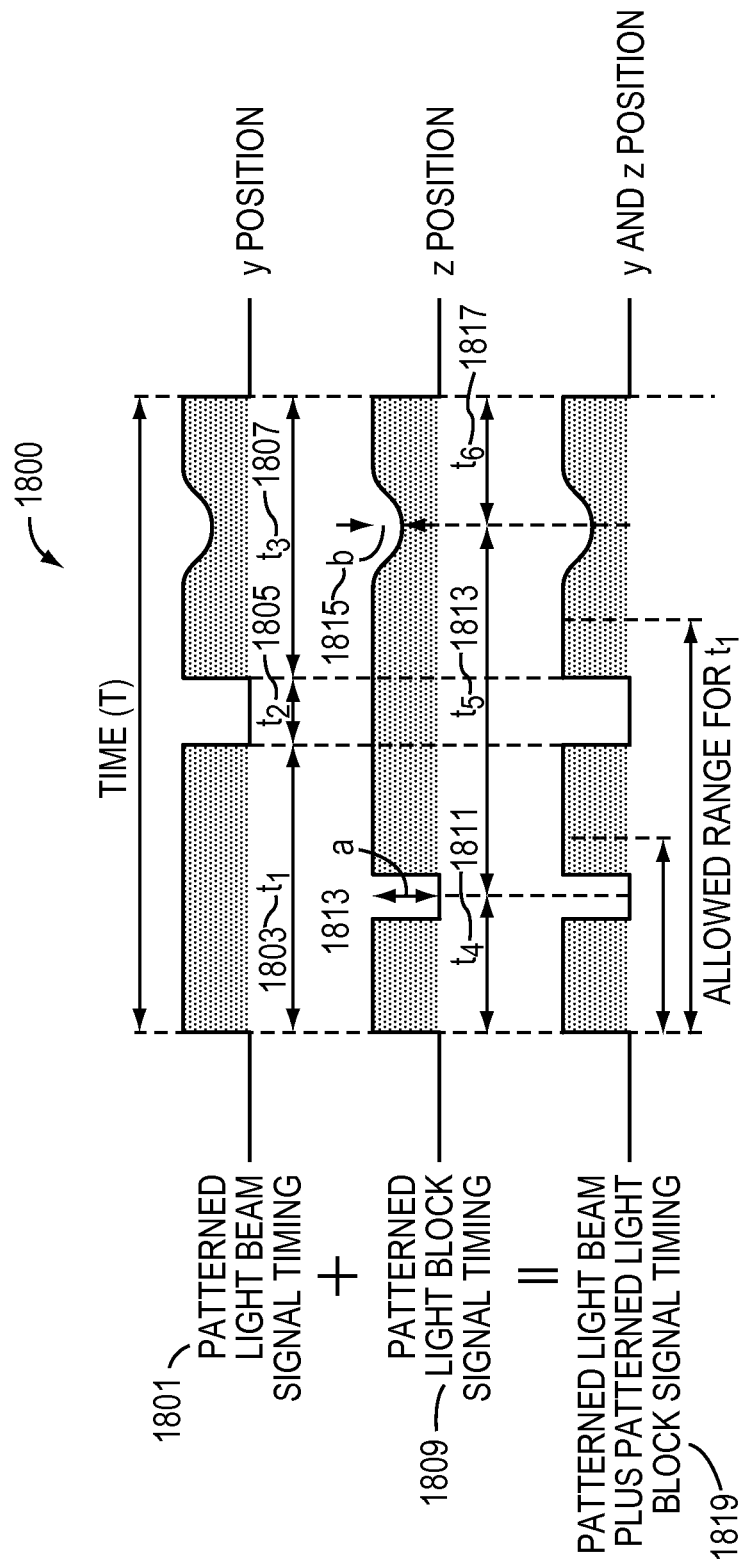
FIG. 18 is a depiction of a measured signal that may be obtained using the system of FIG. 16.

FIG. 18 provides an example of a measurement signal 1819 which may be obtained from the particle detection system of FIG. 16. The resulting measurement signal 1819 may be produced by the addition of the measurement signal obtained from the pattern beam 1801 and the measurement signal obtained from the optical pattern block 1809. Similar to the measurement signal shown in FIG. 5B, the measurement signal obtained from the patterned light beam 1801 may comprise three portions indicative of a time value representing the time the particle passed through the three sections of the pattern beam. In this example, $t_1$ represents the time the particle passed through the first section of the pattern beam, $t_2$ represents the time the particle passed through a second section of the pattern beam, and $t_3$ represents the time taken for the particle to pass through the third section of the pattern beam (FIG. 5A).

The measurement signal obtained by the pattern light block 1809 illustrates an example of a signal obtained from a particle traveling in the top path of the sample volume, as illustrated in FIG. 13B. The exact particle location in the z, or first, dimension may be obtained empirically from the measured signal, for example in a similar manner as was previously described in relation to FIG. 13B. The exact particle location in the z, or first, dimension may also be found quantitatively using the timing values $t_4$-$t_6$, 1811-1817 respectively, and amplitudes a and b, 1813 and 1815 respectively. The quantitative method of finding the particle location in the z, or first dimension may rely not only on the timing values supplied by the temporal profile, but may also rely on the optical system that fouses the scattered light on to the patterned light block.

Figure 19:
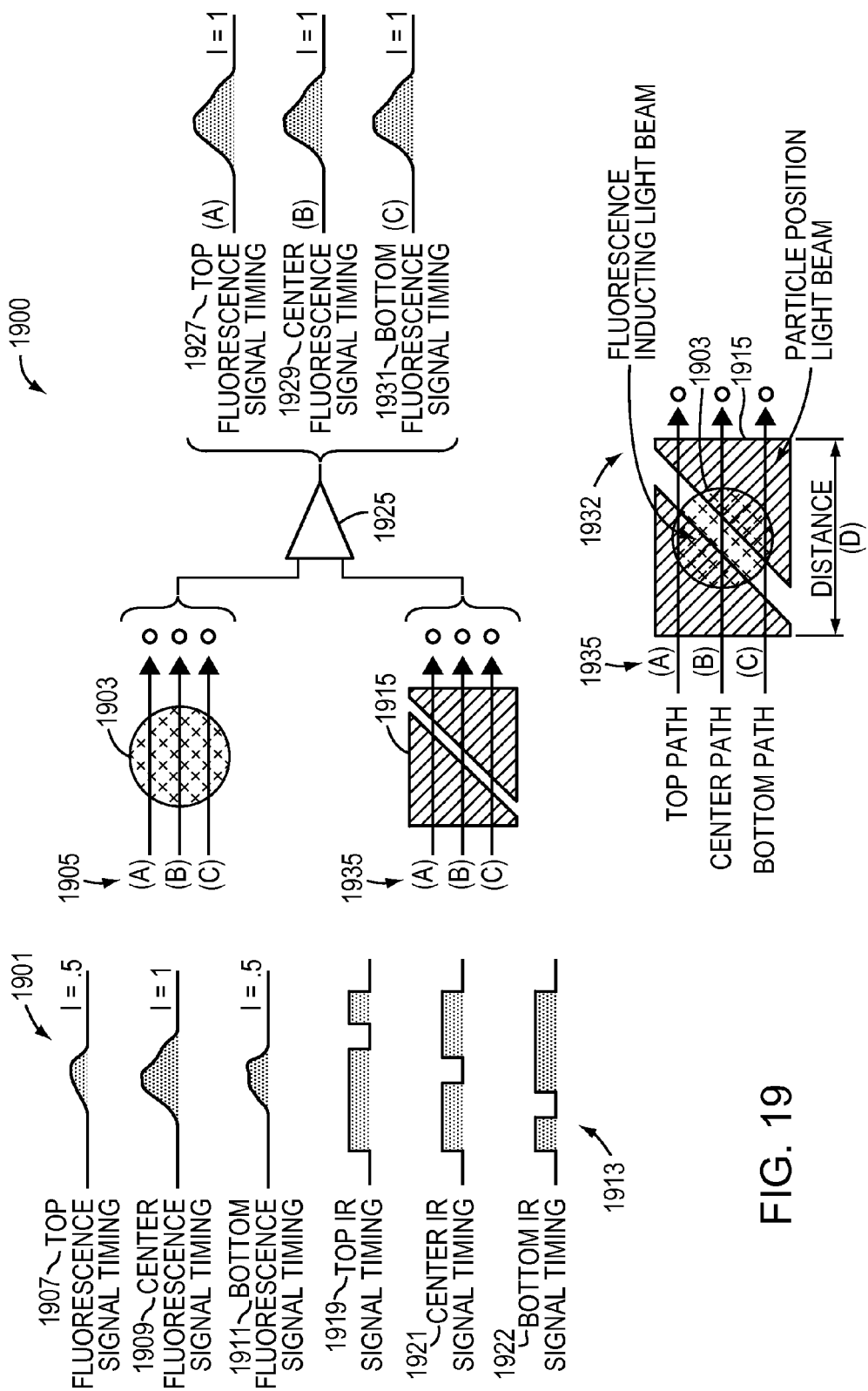
FIG. 19 is a depiction of a measurement normalization (or correction) using a patterned beam particle detection system, according to an embodiment of the present invention.

FIG. 19 illustrates an example application for which the particle position detection system may be used. Region 1901 illustrates a light beam 1903 that induces fluorescence in particles it illuminates and particles traveling in a top 1905a, or a center 1905b, or a bottom 1905c particle path. Fluorescent signals 1907, 1909, and 1911 represent the measured signals obtained from identical particles traveling in the top, center, and bottom paths, respectively. As is shown in the figure, the signal obtained from the particle traveling in the center path 1909 provides the strongest signal, with the integration under the curve equaling, for example, 1.0. In contrast, the signals obtained from the top and bottom paths 1907 and 1911, respectively, show weaker signals with the integration of both curves equaling, for example, 0.5. Thus identical particles traveling through different parts of the fluorescence inducing beam produce different amounts of fluorescence. This nonuniformity in signals confuses the discrimination of different types of particles. For example a big particle traveling through the edge of the fluorescence inducing beam may generate as much fluorescence signal as a small particle traveling through the center of the fluorescence inducing beam Block 1913 represents the pattern beam 1915, and the particle paths 1917a-c, as was previously described in the system shown in FIG. 2. Using the information from the previously described particle detection system, it may be possible to determine where the particle is traveling in the fluorescent beam. As shown in region 1932 the fluorescent beam 1903 may be superimposed with the particle beam 1915, thus, the two obtained measurements may be combined in order to find the exact location of the particle traveling through the fluorescent beam. Using the knowledge of the particle position, a normalization (or correction) factor may be compiled, such that the normalization factor may be multiplied by the weaker signals 1907 and 1911. Therefore, the weaker signals may be normalized so that their integration values equals 1, resulting in a stronger signal reading as shown in the updated signals 1927, 1929 and 1931. Such a calculation may be obtained from a calculation unit 1925. This normalization removes the variation in fluorescence signals due to particle position and allows the remaining variations to be interpreted as variations in particle characteristics.

While this invention has been particularly shown and described with references to example embodiments thereof, it will be understood by those skilled in the art that various changes in form and details may be made therein without departing from the scope of the invention encompassed by the appended claims.

What is claimed is:

1. A method of measuring a position of a particle in a flow, comprising:
   temporally modulating an illumination beam to produce a modulated illumination beam;
   spatially patterning the modulated illumination beam propagating along a first dimension to impart an illumination pattern onto the modulated illumination beam in second and third dimensions, different from the first dimension;
   passing a particle traveling in the second dimension through the modulated illumination beam;
   detecting a temporal profile of scattered light, produced by the particle's passing through the modulated illumination beam; and
   determining the position of the particle in the first dimension based on the temporal profile of the detected scattered light and a geometrical relationship of the illumination pattern.

2. The method of claim 1, wherein the illumination pattern includes a unique spatial pattern of varying light intensity.

3. The method of claim 2, wherein the illumination pattern includes at least one spatial region of zero light intensity.

4. The method of claim 1 further comprising adjusting temporal modulation of the modulated illumination beam.

5. An apparatus for measuring a position of a particle in a flow comprising:
   a light source configured to generate an illumination beam propagating along a first dimension,
   a spatial light modulator, configured to impart an illumination pattern onto the illumination beam in second and third dimensions, different from the first dimension;
   a temporal modulator configured to temporally modulate the illumination beam;
   a detector configured to detect a temporal profile of scattered light produced by a particle's passing through the illumination beam in the second dimension; and
   a processing unit operably coupled to the detector and configured to determine the position of the particle in the first dimension based on the temporal profile of the scattered light and a geometrical relationship of the illumination pattern.

6. The apparatus of claim 5, wherein the spatial light modulator is a masking element in optical arrangement with the light source, configured to impart onto the illumination beam the illumination pattern having a plurality of spatial regions, wherein at least two spatial regions are of varying light intensity.

7. The apparatus of claim 5, wherein the spatial light modulator is a masking element in optical arrangement with the light source, configured to impart onto the illumination beam the illumination pattern having at least one spatial region of zero light intensity.

8. The apparatus of claim 5, wherein the light source is a first light source, the temporal modulator is a first temporal modulator, the illumination beam is a first illumination beam, the illumination pattern is a first illumination pattern, the temporal profile is a first temporal profile, and the scattered light is a first scattered light, the apparatus further comprising:
- a second light source configured to generate a second illumination beam propagating along the third dimension;
- a second spatial light modulator, configured to impart a second illumination pattern onto the second illumination beam in the first and the second dimensions; and
- a second temporal modulator configured to temporally modulate the second illumination beam.

9. The apparatus of claim 8, wherein the first and second temporal modulators are configured to temporally modulate the first and second illumination beams at first and second frequencies, respectively.

10. The apparatus of claim 8, wherein the first and second illumination beams each includes light of first and second wavelengths, respectively.

11. The apparatus of claim 10, wherein the detector is a first detector, the apparatus further comprising:
- a second detector operably coupled to the processor and configured to detect a second temporal profile of second scattered light produced by the particle's passing through the second illumination beam; and
- a first filter configured to reflect the first scattered light and to transmit the second scattered light and to prevent the second scattered light from illuminating the first detector.

12. The apparatus of claim 11, further comprising:
- a second filter configured to prevent the first scattered light from illuminating the second detector.

13. The apparatus of claim 8, wherein the processing unit is further configured to adjust settings of the first and second temporal modulators.

14. The apparatus of claim 8, wherein the first and second temporal modulator each is further configured to report its corresponding current modulation setting.

* * * * *